US011473055B2

(12) United States Patent
Maghodia et al.

(10) Patent No.: US 11,473,055 B2
(45) Date of Patent: Oct. 18, 2022

(54) VIRUS-FREE CELL LINES AND METHODS FOR OBTAINING SAME

(71) Applicant: Glycobac, LLC, Laramie, WY (US)

(72) Inventors: Ajay Maghodia, Laramie, WY (US); Christoph Geisler, Laramie, WY (US); Donald Jarvis, Laramie, WY (US)

(73) Assignee: GLYCOBAC, LLC, Laramie, WY (US)

( * ) Notice: Subject to any disclaimer, the term of this patent is extended or adjusted under 35 U.S.C. 154(b) by 350 days.

(21) Appl. No.: 15/772,476

(22) PCT Filed: Nov. 1, 2016

(86) PCT No.: PCT/US2016/059857
§ 371 (c)(1),
(2) Date: Apr. 30, 2018

(87) PCT Pub. No.: WO2017/075627
PCT Pub. Date: May 4, 2017

(65) Prior Publication Data
US 2018/0355311 A1 Dec. 13, 2018

Related U.S. Application Data

(60) Provisional application No. 62/249,288, filed on Nov. 1, 2015.

(51) Int. Cl.
*C12N 5/07* (2010.01)
*C12N 15/00* (2006.01)
*C12N 7/00* (2006.01)

(52) U.S. Cl.
CPC ............. *C12N 5/0601* (2013.01); *C12N 7/00* (2013.01); *C12N 15/00* (2013.01); *C12N 2500/40* (2013.01); *C12N 2710/14151* (2013.01); *C12N 2760/20011* (2013.01); *C12N 2770/30011* (2013.01)

(58) Field of Classification Search
CPC ............. C12N 5/0601; C12N 2500/40; C12N 2760/20011; C12N 2760/20021; C12N 5/0081
See application file for complete search history.

(56) References Cited

U.S. PATENT DOCUMENTS

2009/0239830 A1 9/2009 Josh et al.
2013/0095135 A1 4/2013 Collignon et al.
2016/0244487 A1 8/2016 Haynes
2017/0202948 A1 † 7/2017 Smith

FOREIGN PATENT DOCUMENTS

JP 2010-538968 A 12/2010
JP 2013-531503 A 8/2013
WO 1997/007674 A1 † 3/1997
WO 2002/092139 A1 † 11/2002
WO 2015/051255 A1 † 4/2015
WO 2016/154338 A1 † 9/2016
WO WO2017/075627 A1 5/2017
WO 2017/161151 A1 † 9/2017

OTHER PUBLICATIONS

Crawford et al. Persistent baculovirus infections: Spodoptera frugiperda NPV and Autographa californica NPV in Spodoptera frugiperda cells. Archives of Virology, vol. 78, pp. 65-79, 1983. (Year: 1983).*
De La Torre et al. Ribavirin cures cells of a persistent infection with foot-and-mouth disease virus in vitro. Journal of Virology, vol. 61, No. 1, pp. 233-235, Jan. 1987. (Year: 1987).*
Kim et al. Enhanced inhibition of foot-and-mouth disease virus by combinations of porcine interferon-α and antiviral agents. Antiviral Research, vol. 96, pp. 213-220, 2012. (Year: 2012).*
Pohjala et al. Inhibitors of alphavirus entry and replication identified with astable Chikungunya replicon cell line and virus-based assays. PLoS ONE, vol. 6, No. 12, e28923, Dec. 19, 2011, printed as pp. 1-13. (Year: 2011).*
Konstantinova et al. Ribavirin: Biotechnological synthesis and effect on the reproduction of Vaccinia virus. Russian Journal of Bioorganic Chemistry, vol. 30, No. 6, pp. 553-560, 2004. (Year: 2004).*
Garcia et al. Quantitative real-time PCR detection of rift valley fever virus and its application to evaluation of antiviral compounds. Journal of Clinical Microbiology, vol. 39, No. 12, pp. 4456-4461, Dec. 2001. (Year: 2001).*
Portner et al. (Measles virus ribonucleic acid and protein synthesis: Effects of 6-azauridine and cycloheximide on viral replication. Journal of Virology, vol. 11, No. 1, pp. 46-53, Jan. 1973. (Year: 1973).*
Ogura et al. Establishment and characterization of a virus-free chick cell line. Acta Med Okayama, vol. 41, No. 3, pp. 141-143, 1987. (Year: 1987).*
Thomas et al. The application and mechanism of action of ribavirin in therapy of hepatitis C. Antiviral Chemistry and Chemotherapy, vol. 23, pp. 1-12, 2012. (Year: 2012).*
Crawford et al. Persistent baculovirus infections: Spodoptera frugiperda NPV and Autographs californica NPV in Spodoptera frugiperda Cells. Archives of Virology, vol. 78, pp. 65-79, 1983. (Year: 1983).*

(Continued)

*Primary Examiner* — Jennifer Dunston
(74) *Attorney, Agent, or Firm* — Sigma-Aldrich Co. LLC

(57) ABSTRACT

The current teachings are directed to virus free cells lines derived from virus-contaminated starting material, such as an organism or a cell line. Methods for obtaining virus free cell lines obtained from virus-contaminated starting material are also provided. Exemplary virus free cell lines include: cell lines derived from a *Spodoptera frugiperda* cell line contaminated with Sf-rhabdovirus, wherein the cell lines lack Sf-rhabdovirus; and cell lines derived from a *Trichoplusia ni* cell line contaminated with an alphanodavirus, wherein the cell line lacks an alphanodavirus.

4 Claims, 23 Drawing Sheets

Specification includes a Sequence Listing.

(56) References Cited

OTHER PUBLICATIONS

De Clerq, E. Antiviral agents: Characteristic activity spectrum depending upon the molecular target with which they interact. Advances in Virus Research, vol. 42, pp. 1-55, 1993. (Year: 1993).*
Bussereau et al. Search for compounds which have an inhibitory effect on rhabdovirus multiplication in vitro. Annales de l'Institut Pasteur/Virologie, vol. 134, No. 1, pp. 127-134, 1983 (Year: 1983).*
Hashimoto et al., Ao38, a new cell line from eggs of the black witch moth, *Ascalapha odorata* (Lepidoptera: Noctuidae), is permissive for AcMNPV infectino and produces high levels of recombinant proteins, BMC Biotechnol, Jul. 6, 2010, vol. 10, No. 50, pp. 1-16, abstract, p. 2 col. 1 para 1, p. 2 col. 1 para2, p. 2 col. 1 para 3, p. 2 col. 1 para 4—col. 2 para 1, p. 3 col. 1 para 3, p. 3 col. 2 para 2, p. 11 col. 2 para 2.
Hashimoto et al., BTI-Tnao38, a new cell line derived from Trichoplusia ni, is permissive for AcMNPV infection and produces high levels of recombinant proteins. BMC Biotechnol., Apr. 24, 2012, vol. 12, No. 12, pp. 1-4, abstract, p. 1 col. 2 para 1, p. 3 col. 1 para 2.
Geisler et al., Engineering .beta. 1,4-galactosyltransferase I to reduce secretion and enhance N-glycan elongation n insect cells. J Biotechnol., Jan. 10, 2015, vol. 193, pp. 52-65, p. 52 col. 2 para 2, p. 54 col. 1 para 2, p. 54 col. 2 para 1.
Ma et al., Identification of a novel rhabdovirus in Spodoptera frugiperda cell lines. J Virol., Jun. 2014, vol. 88, No. 12, pp. 6576-6585, p. 6584 col. 1 para 1, p. 6584 col. 1 para 2.
ISR/Written Opinion for PCT/US2016/059857 (parent application), 9 pages, dated Mar. 3, 2017.
IPRP for PCT/US2016/059857 (parent application), 6 pages, dated Mar. 3, 2017.
Chen et al. The transcriptome of the Baculovirus Autographa californica multiple nucleopolyhedrovirus in Trichoplusia ni cells. Journal of Virology. Jun. 2013, vol. 87, pp. 6391-6405.
Database Genbank, "Alkaline Phosphatase, Placental Type Preproprotein [*Homo sapiens*]", NCBI Reference Sequence: NP 001623.3, Jan. 18, 2021, pp. 1-4.
Database Genbank, "Erythropoietin Precursor [*Homo sapiens*]", NCBI Reference Sequence: NP 000790.2, Dec. 27, 2020, pp. 1-3.
Database Genbank et al., "Spodoptera Frugiperda Rhabdovirus Isolate Sf, Complete Genome", NCBI Reference Sequence: NC_025382. 1, Aug. 13, 2018, pp. 1-6.
Database Genbank, "TSA: Spodoptera Frugiperda, Transcriptome Shotgun Assembly", GenBank: GESP00000000.1, Jun. 27, 2016, pp. 1-2.
Kakumani et al., "De Novo Transcriptome Assembly and Analysis of Sf21 Cells Using Illumina Paired", Biology Direct, vol. 10, No. 44, 2015, pp. 1-8.
Li et al., "Latent Infection of a New Alphanodavirus in an Insect Cell Line", Journal of Virology, vol. 81, No. 20, Oct. 2007, pp. 10890-10896.
Margalith et al., "Transformation of BSC 1 Cells following Chronic Infection with SV40", Journal of General Virology, vol. 5, No. 3, Apr. 24, 1969, pp. 321-327.
Rada et al., "Antiviral Action and Selectivity of 6-Azauridine", Annals of the New York Academy of Sciences, vol. 284, Mar. 4, 1977, pp. 410-417.
Saulnier et al., "Complete Cure of Persistent Virus Infections byAntiviral siRNAs", Molecular Therapy, vol. 13, No. 1, Jan. 2006, pp. 142-150.
Hallun Ma et al., Identification of a Novel Rhabdovirus in Spodoptera frugiperda Cell Lines, pp. 6576-6585, J. Virol. 88(12), 2014.†
Nobuko Nakai, Detection and Elimination of Contaminating Microorganisms in Transplantable Tumors and Cell Lines, pp. 309-313, Exp. Anim. 49(4) 2000.†
Guidance for Industry: Characterization and Qualification of Cell Substrates and Other Biological Materials Used in the Production of Viral Vaccines for Infectious Disease Indications, pp. 1-50, U.S. Dept. of Health and Human Servs. Food and Drug Admin., Center for Biologics for Evaluation and Research, Feb. 2010.†
A.A. Morley et al., Cloning of Human Lymphocytes Using Limiting Dilution, pp. 418-424, Exp. Hematol. vol. 11 No. 5, May 1983, Intl Society for Experimental Hematology.†
Steven A Fuller et al., Cloning of Hybridoma Cell Lines by Limiting Dilution, pp. 1-2, Unit 11.8 in Current Protocols in Molecular Biology, John Wiley & Sons Inc.†
Christopher Geisler et al., "Rhabdovirus-like endogenous viral elements in the genome of Spodoptera frugiperda insect cells are actively transcribed: Implications for adventitious virus detection," pp. 219-225, Biologicals 44 (2016), Elsevier.†
Yoshifumi Hashimoto et al., "Ao38, a new cell line from eggs of the black witch moth, *Ascalapha odorata* (Lepidoptera: Noctuidae), is permissive for AcMNPV infection and produces high levels of recombinant proteins," pp. 1-16, BMC Biotechnology 12 (12) 2010.†
J. L. Vaughn et al., "The establishment of two cell lines from the insect *Spodoptera frugiperda* (lepidoptera; noctuidae)," pp. 213-217, In Vitro (vol. 13, No. 4) 1977.†
Yoshifumi Hashimoto et al., "Complete study demonstrating the absence of rhabdovirus in a distinct Sf9 cell line," pp. 1-17, PLoS ONE 12(4), Apr. 19, 2017.†

* cited by examiner
† cited by third party

```
                           SEQUENCE LISTING

<160> NUMBER OF SEQ ID NOS: 28

<210> SEQ ID NO 1
    <211> LENGTH: 25
    <212> TYPE: DNA
    <213> ORGANISM: Spodoptera frugiperda rhabdovirus

<400> SEQUENCE: 1
ggcaaggctg tttggattac tgacc                                              25

<210> SEQ ID NO 2
    <211> LENGTH: 24
    <212> TYPE: DNA
    <213> ORGANISM: Spodoptera frugiperda rhabdovirus

<400> SEQUENCE: 2
acaggtttgc agctaaggag gaca                                               24

<210> SEQ ID NO 3
    <211> LENGTH: 24
    <212> TYPE: DNA
    <213> ORGANISM: Spodoptera frugiperda rhabdovirus

<400> SEQUENCE: 3
tggcgaggga ctgcttacag aagg                                               24

<210> SEQ ID NO 4
    <211> LENGTH: 20
    <212> TYPE: DNA
    <213> ORGANISM: Spodoptera frugiperda rhabdovirus

<400> SEQUENCE: 4
cacagccggg ggtgcaatca                                                    20

<210> SEQ ID NO 5
    <211> LENGTH: 23
    <212> TYPE: DNA
    <213> ORGANISM: Spodoptera frugiperda rhabdovirus

<400> SEQUENCE: 5
acaggagatg cggaagaccc ctc                                                23

<210> SEQ ID NO 6
    <211> LENGTH: 22
    <212> TYPE: DNA
    <213> ORGANISM: Spodoptera frugiperda rhabdovirus
```

```
<400> SEQUENCE: 6
atctcgcagg tgggacaacc cc                                              22

<210> SEQ ID NO 7
<211> LENGTH: 25
<212> TYPE: DNA
<213> ORGANISM: Spodoptera frugiperda rhabdovirus

<400> SEQUENCE: 7
atatgagagc cccagacaca cagcc                                           25

<210> SEQ ID NO 8
<211> LENGTH: 26
<212> TYPE: DNA
<213> ORGANISM: Spodoptera frugiperda rhabdovirus

<400> SEQUENCE: 8
acgatgtggt gagagaaaca cctcct                                          26

<210> SEQ ID NO 9
<211> LENGTH: 21
<212> TYPE: DNA
<213> ORGANISM: Spodoptera frugiperda rhabdovirus

<400> SEQUENCE: 9
cacatctaga gcttgaagac c                                               21

<210> SEQ ID NO 10
<211> LENGTH: 19
<212> TYPE: DNA
<213> ORGANISM: Spodoptera frugiperda rhabdovirus

<400> SEQUENCE: 10
accatcacag ccagtgctg                                                  19

<210> SEQ ID NO 11
<211> LENGTH: 18
<212> TYPE: DNA
<213> ORGANISM: Spodoptera frugiperda rhabdovirus

<400> SEQUENCE: 11
gagtgttgat acatgtcg                                                   18

<210> SEQ ID NO 12
<211> LENGTH: 18
<212> TYPE: DNA
<213> ORGANISM: Spodoptera frugiperda rhabdovirus

<400> SEQUENCE: 12
gtgaccaacc tcttccag                                                   18

<210> SEQ ID NO 13
<211> LENGTH: 19
<212> TYPE: DNA
<213> ORGANISM: Spodoptera frugiperda rhabdovirus

<400> SEQUENCE: 13
gctctagtgt gcgactgtg                                                  19

<210> SEQ ID NO 14
<211> LENGTH: 20
<212> TYPE: DNA
<213> ORGANISM: Spodoptera frugiperda rhabdovirus
```

```
<400> SEQUENCE: 14
gctcagacag gttcttattg                                               20

<210> SEQ ID NO 15
<211> LENGTH: 20
<212> TYPE: DNA
<213> ORGANISM: Spodoptera frugiperda rhabdovirus

<400> SEQUENCE: 15
gttgaaccct aggagaactc                                               20

<210> SEQ ID NO 16
<211> LENGTH: 18
<212> TYPE: DNA
<213> ORGANISM: Spodoptera frugiperda rhabdovirus

<400> SEQUENCE: 16
gtatgcaggt ggttgagg                                                 18

<210> SEQ ID NO 17
<211> LENGTH: 20
<212> TYPE: DNA
<213> ORGANISM: Spodoptera frugiperda rhabdovirus

<400> SEQUENCE: 17
gctccaatcc tctctcctat                                               20

<210> SEQ ID NO 18
<211> LENGTH: 18
<212> TYPE: DNA
<213> ORGANISM: Spodoptera frugiperda rhabdovirus

<400> SEQUENCE: 18
gactgagagg gaactcaa                                                 18

<210> SEQ ID NO 19
<211> LENGTH: 25
<212> TYPE: DNA
<213> ORGANISM: Alphanodavirus sp.

<400> SEQUENCE: 19
gggaaccgag ttacacgcgc attgc                                         25

<210> SEQ ID NO 20
<211> LENGTH: 28
<212> TYPE: DNA
<213> ORGANISM: Alphanodavirus sp.

<400> SEQUENCE: 20
ccgccctaag ttgtagttgt tgggacgg                                      28

<210> SEQ ID NO 21
<211> LENGTH: 21
<212> TYPE: DNA
<213> ORGANISM: Alphanodavirus sp.

<400> SEQUENCE: 21
gatgctgact caccattcac c                                             21

<210> SEQ ID NO 22
<211> LENGTH: 26
<212> TYPE: DNA
```

```
<213> ORGANISM: Alphanodavirus sp.

<400> SEQUENCE: 22
ccgataagcc tagcgttgac agattg                                              26

<210> SEQ ID NO 23
<211> LENGTH: 21
<212> TYPE: DNA
<213> ORGANISM: Alphanodavirus sp.

<400> SEQUENCE: 23
gccttcgcac cacctgactt c                                                   21

<210> SEQ ID NO 24
<211> LENGTH: 24
<212> TYPE: DNA
<213> ORGANISM: Alphanodavirus sp.

<400> SEQUENCE: 24
gccaggaatg ttgcttgcaa cagc                                                24

<210> SEQ ID NO 25
<211> LENGTH: 22
<212> TYPE: DNA
<213> ORGANISM: Alphanodavirus sp.

<400> SEQUENCE: 25
catccagatc cgatcaagtg tc                                                  22

<210> SEQ ID NO 26
<211> LENGTH: 20
<212> TYPE: DNA
<213> ORGANISM: Alphanodavirus sp.

<400> SEQUENCE: 26
cacggatgac aatggtgtcc                                                     20

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 27

His His His His His His His His
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Asn Leu Tyr Phe Gln Gly
1               5
```

VIRUS-FREE CELL LINES AND METHODS FOR OBTAINING SAME

CROSS-REFERENCE TO RELATED APPLICATIONS

This application claims priority to International Application Serial No. PCT/US16/59587, filed Nov. 1, 2016, and U.S. Provisional Application Ser. No. 62/249,288 filed Nov. 1, 2015, both of which are incorporated herein by reference in their entirety.

STATEMENT REGARDING FEDERALLY SPONSORED RESEARCH

This work was performed in part with government support under National Institutes of Health Grants NIH R43 GM102982 and NIH R43 AI112118. The U.S. Government may have certain rights in the claimed inventions.

SEQUENCE LISTING

This application contains a Sequence Listing that has been submitted in ASCII Format via EFS-Web and is hereby incorporated by reference in its entirety. The ASCII copy, created on Sep. 24, 2020, is named P15-282_US-PCT_SL.txt and is 4,887 bytes in size.

FIELD

The current teachings generally relate to continuous cell lines that are free from contaminating virus. The current teachings also relate to methods for obtaining virus free cell lines that are derived from cells or organisms that are contaminated with virus.

BACKGROUND

Cells propagated in vitro can be broadly categorized as either primary cells or continuous cell lines, also referred to as an established cell line. Primary cells may be obtained by isolating an organ or tissue from an organism and disaggregating it to create a mixture of individual cells. When primary cells are propagated in culture, they divide only a limited number of times before losing their ability to proliferate, a genetically determined event known as senescence. Some cells, however, undergo a process called transformation and acquire the ability to divide indefinitely. These cells are referred as transformed cells or continuous cells. Compared to the naturally occurring cells found in the tissue or organ from which they were derived, continuous cell lines typically have genetic abnormalities such as aneuploidy or heteroploidy, and lack contact inhibition and anchorage dependence often seen with primary cells.

Over the years, it has been repeatedly discovered that cultured cells used for bioproduction are contaminated with viruses. For example, in the early 1960s, it was discovered that adenovirus vaccines and poliovirus vaccines that were produced in primary Rhesus monkey kidney (RMK) cells were contaminated with simian virus 40 (SV40). It was subsequently shown that SV40 caused tumors in hamsters and that antibodies to SV40 were detected in people who had received inactivated poliovirus vaccine produced in primary RMK cells. In the 1970s it was discovered that several lots of live measles, mumps, rubella, and polio vaccines were contaminated with bacterial viruses known as bacteriophages. Avian Leukosis Virus (ALV) and endogenous avian virus (AEV) were found in attenuated vaccines for yellow fever, measles, and mumps produced in chicken embryo fibroblast cells. The source for the vaccine-associated ALV and AEV was thought to be endogenous retroviruses integrated in the chicken genome. More recently, several lots of rotavirus vaccine were found to be contaminated with infectious porcine circovirus-1 (PCV-1).

Since it was first described in the peer-reviewed literature in the early 1980's, the baculovirus-insect cell system (BIGS) has become a widely recognized and heavily utilized recombinant protein production platform. The advantages of the BIGS include its flexibility, speed, simplicity, eukaryotic protein processing capabilities, and ability to produce multi-subunit protein complexes. For nearly 30 years, the BIGS was used mainly to produce recombinant proteins for basic research in academic and industrial labs. More recently, however, the BIGS emerged as a bona fide commercial manufacturing platform, which is now being used to produce several biologics licensed for use in human (CERVARIX®, PROVENGE®, GLYBERA® and FLUBLOK®) or veterinary (PORCILIS® PESTI, BAYOVAC CSF E2®, CIRCUMVENT® PCV, INGELVAC CIRCOFLEX® and PORCILIS® PCV) medicine. In addition, the BIGS is being used to produce several other biologics, including noroviral, parvoviral, Ebola viral, respiratory syncytial viral, and hepatitis E viral vaccine candidates in various stages of human clinical trials.

The insect cell lines most commonly used as hosts in the BIGS are derived from the cabbage looper, *Trichoplusia ni* (Tn), or fall armyworm, *Spodoptera frugiperda* (Sf), and most biologics manufactured with the BIGS are produced using the latter. The original Sf cell line, designated IPLB-SF-21, also known as Sf-21, was derived from pupal ovaries in 1977. Other commonly used Sf cell lines include Sf9 (a subclone of IPLB-SF-21), and its daughter subclones, including Super 9 and Sf900+, also known as EXPRESSF+®. The original Tn cell line, designated TN-368, was derived from ovarian tissue isolated from newly emerged virgin female moths, as reported by Hink in 1970. Other commonly used Tn cell lines include BTI-Tn-5B1-4 (commercialized as HIGH FIVE™) and Tni PRO cells.

In 2007, a group of scientists from Japan and New Zealand discovered BTI-Tn-5B1-4 cells are contaminated with a novel nodavirus (Li et al., J. Viral. 81:10890-96), designated herein "Tn-nodavirus." We confirmed and extended this finding when we found all our lab Tn cell lines, including TN-368, BTI-Tn-5B1-4, and Tni PRO, were contaminated with this virus. Subsequently, in 2014, scientists at the U.S. FDA's Center for Biologics Research and Evaluation (CBER) found that every Sf cell line tested, including Sf-21 and Sf9 cells obtained from two reputable commercial sources, were contaminated with a rhabdovirus, now known as Sf-rhabdovirus (Ma et al., J. Viral. 88: 6576-85, 2014). A research group at Takeda Vaccines, Inc. independently confirmed the presence of Sf-rhabdovirus in the Sf9 cells used to produce their norovirus vaccine candidate (Takeda Vaccines, Inc., U.S. Patent Application Publication No. US 2016/0244487; PCT/US14/59060). In addition, we found all our lab Sf cell lines, including Sf-21, Sf9, and EXPRESSF+®, obtained from a variety of sources, were contaminated with this virus.

There exists a need for cell lines that are free of contaminating virus and for methods for generating virus free cell lines obtained from virus infected cell lines or organisms that are persistently infected or contain an endogenous virus.

SUMMARY

The current teachings are directed to established cell lines derived from virus-contaminated cells or organisms, wherein the cell line is characterized by a lack of virus while retaining relevant cellular functions. Such established cell lines are particularly useful as components of biological platforms used for production of vaccines, recombinant proteins and biologics for human and veterinary use, for example, the BIGS. The current teachings are also directed to methods for obtaining virus-free established cell lines from cells contaminated with virus or organisms that are contaminated with virus, for example but not limited to a persistent infection or due to endogenous virus.

According to one exemplary embodiment, an established insect cell line is directly or indirectly obtained from the fall armyworm, *Spodoptera frugiperda*. This cell line is characterized by a lack of Sf-rhabdovirus, unlike Sf9 cells and the fall armyworm, from which the Sf9 cell line was derived. When compared to the Sf9 cell line, the cells of this exemplary established cell line: grow to the same or very similar cell densities in culture, have the same or very similar cell diameters (size), have the same or very similar doubling times (growth rate), and produce similar N-glycosylation patterns. The cells of this novel established cell line are functionally different from Sf9 cells in that they produce more infectious recombinant baculovirus particles with AcP(−)p6.9hEPO or AcP(−)p6.9hSEAP and are not contaminated with Sf-rhabdovirus. This novel established cell line is further characterized by being structurally (genetically) different from *Spodoptera frugiperda* and Sf-21 cells, from which Sf9 cells were derived.

According to certain cell line embodiments, an exemplary established cell line, characterized by a lack of virus, is derived from a virus-contaminated organism or virus-contaminated cells. In certain embodiments, the cell line is derived from a virus-contaminated *Trichoplusia ni* cell. In certain embodiments, the *Trichoplusia ni* cell line is the TN-368 cell line. In certain embodiments, the virus is an alphanodavirus. According to certain embodiments, the cell line is further characterized by a cell density, an average cell diameter, a morphology, and a N-glycosylation pattern that is the same or substantially the same as TN-368 cells when the cell line and the TN-368 cells are propagated under the same conditions.

According to another exemplary established cell line embodiment, an insect cell line is directly or indirectly obtained from the cabbage looper, *Trichoplusia ni*. This cell line is characterized by a lack of nodavirus, unlike TN-368 cells, derived from *Trichoplusia ni*. When compared to the TN-368 cell line, the cells of this exemplary established cell line: grow to the same or very similar cell densities in culture, have the same or very similar cell diameters (size), and produce similar N-glycosylation patterns.

According to an exemplary method for obtaining a virus free cell line derived from a virus-contaminated organism or virus-contaminated cells comprises: isolating a cell from a virus-contaminated organism or from virus-contaminated cells; combining the isolated cell with a cell culture media comprising an antiviral compound to form a first culture composition; incubating the first culture composition under conditions suitable for the cell to grow and divide, thereby generating a multiplicity of cells; removing a portion of the multiplicity of cells or the cell culture media and testing for the presence or absence of a virus; combining at least some of the multiplicity of cells with cell culture media without an antiviral compound to form a second culture composition; and incubating the second culture composition under conditions suitable for the cells to grow and divide, thereby obtaining a virus free cell line.

According to certain exemplary methods, an established cell line is obtained by isolating a single cell or small number of cells from virus infected primary cells, a cell line contaminated with virus, or a contaminated organism. The isolated cell(s) are combined with cell culture media that contains an antiviral compound, forming a first culture composition. The first culture composition is incubated under conditions that allow the cells to grow and divide, thereby generating a multiplicity of cells. The culture media is periodically replaced with fresh culture media that contains the antiviral compound. A small number of cells obtained from the first culture composition or a volume of culture media obtained from the first culture composition is tested for the presence or absence of virus. When no viral nucleic acid is detected, at least some of the cells from the first culture composition are combined with culture media without the antiviral compound to form a second culture composition. The second culture composition is incubated under conditions that allow the cells to grow and divide and the culture media is periodically replaced with fresh culture media. In certain embodiments, as the cells continue to grow, the number of cells increases and the cells are expanded from one growth container to multiple containers, including when the cells are periodically split (also known as passaging). In certain embodiments, a sample of cells or culture media from at least one growth container is tested for the presence or absence of viral nucleic acid, an indicator for the presence of virus. Once the number of cells has reached a sufficient quantity, aliquots of cells may be frozen or stored using known methods.

BRIEF DESCRIPTION OF THE FIGURES

These and other features and advantages of the current teachings will become better understood with regard to the following description, appended claims, and accompanying figures. The skilled artisan will understand that the figures, described below, are for illustration purposes only and are not intended to limit the scope of the disclosed teachings in any way.

As shown in FIG. 3C, an Sf-rhabdovirus amplicon was observed in the lanes corresponding to RNA isolated from Sf9 cells and RNA isolated from the Sf9 cell-free media pellet (FIG. 3C, lanes Sf9 and Sf9 CFM, respectively). In contrast, the Sf-rhabdovirus amplicon was not detected in the RNA isolated from the Sf-RVN cell-free media pellet (FIG. 3C, lane Sf-RVN CFM). All results shown in FIGS. 3A-3C were obtained using RNA from cells that were cultivated in the absence of antiviral drugs. RNAs extracted from Sf9 cells and from the pellet obtained by ultracentrifuging Sf9 CFM were used as positive controls; and RNA extracted from S2R+ cells (S2) were used as negative controls. An additional negative control reaction was performed with no template (H2O) and the lanes marked M show the 100-bp markers, with selected sizes indicated on the left.

As shown in FIG. 15C, a Tn-nodavirus amplicon was observed in the lanes corresponding to RNA isolated from TN-368 cells and RNA isolated from the TN-368 cell-free media pellet (FIG. 15C, lanes TN-368 and TN-368 CFM, respectively). In contrast, the Tn-nodavirus amplicon was not detected in the RNA isolated from the Tn-NVN cell-free media pellet. Again, all results shown in FIG. 15A-15C were obtained using RNA from cells cultivated in the absence of antiviral drugs. RNAs extracted from TN-368 cells and from the pellet obtained by ultracentrifuging TN-368 cell-free media (CFM) were used as positive controls and RNA extracted from Sf9 cells were used as negative controls. An additional negative control reaction was performed with no template (H2O) and the lanes marked M show the 100-bp markers, with selected sizes indicated on the left.

FIG. 19A). One set of cell-free media was also used to measure total extracellular hSEAP production levels by immunoblotting analysis (FIG. 19B), with scanning laser densitometry (FIG. 19C) to estimate relative immunoreactive band densities.

DETAILED DESCRIPTION OF CERTAIN EXEMPLARY EMBODIMENTS

Figure 1A:
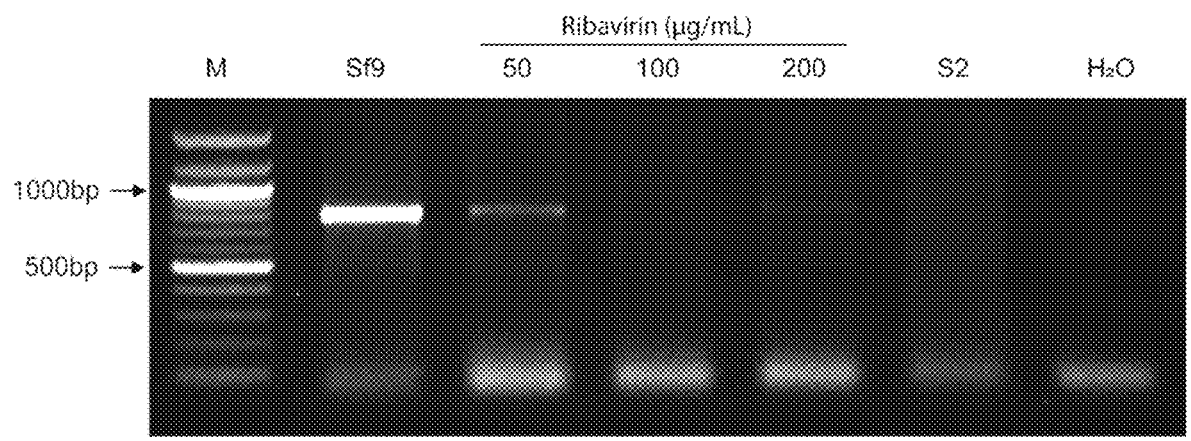
FIGS. 1A-1C: Sf-rhabdovirus in polyclonal Sf9 cells treated with antiviral drug. Polyclonal Sf9 cell populations were treated for about a month with various concentrations of ribavirin (FIGS. 1A and 1B) or ribavirin, 6-azauridine, and vidarabine (FIG. 1C), and then total RNA was extracted and tested for Sf-rhabdovirus RNA by RT-PCR, as described in Example 4. The results shown in FIGS. 1A and 1C were obtained using RNA from cells that were still being cultivated in the presence of antiviral drugs, whereas those shown in FIG. 1B were obtained using RNA from cells that had been treated with ribavirin, but then passaged 12 times in the absence of antiviral drugs, as described in Example 2. Total RNAs extracted from Sf9 cells or *Drosophila melanogaster* S2R+ cells ("S2" in FIGS. 1A-1C, 2A-2B, 3A-3C) were used as the positive and negative controls, respectively. An additional negative control reaction was performed with no template (H2O). Lanes marked "M" show the 100-bp markers, with selected sizes indicated on the left.

It is to be understood that both the foregoing general description and the following detailed descriptions are illustrative and exemplary only and are not intended to limit the scope of the disclosed teachings. The section headings used herein are for organizational purposes only and are not to be construed as limiting the subject matter of the disclosed teachings.

In the Summary above, the Detailed Description, the accompanying Figures, and the claims below, reference is made to particular features (including method steps) of the current teachings. It is to be understood that the disclosure in this specification includes possible combinations of such particular features. For example but not limited to, where a particular feature is disclosed in the context of a particular embodiment of the current teachings, or a particular claim, that feature may also be used, to the extent possible, in combination with and/or in the context of other particular embodiments, and in the current teachings in general.

Where reference is made to a method comprising two or more combined steps, the defined steps can be performed in any order or simultaneously (except where the context excludes that possibility), and the method may include one or more additional steps which are carried out before any of the defined steps, between two of the defined steps, or after all of the defined steps (except where the context excludes that possibility).

Definitions

The term "cell line", used in reference to the current teachings means a population of cells that were expanded from one or a few common ancestor cells, for example but not limited to, a clonal population of cells that have been expanded from a single isolated cell. An "established cell line" is a cell line that has the potential to proliferate indefinitely when given fresh culture media, space to grow, and when incubated under suitable conditions. Such cell lines have undergone changes in vitro (for example but not limited to transformation, chromosomal changes, or both) compared to the naturally-occurring counterpart cell found in the organism. A cell line that is obtained by isolating a single cell from a first cell line, then expanding the isolated cell to obtain a multiplicity of cells to obtain a second cell line, is sometimes referred to as a "subclone" of the first cell line from which it was derived.

As used herein, the term "comprising", which is synonymous with "including" or "characterized by", and cognates of each (such as comprises and includes), is inclusive or open-ended and does not exclude additional unrecited components, elements, or method steps, that is other components, steps, etc., are optionally present. For example but not limited to, an article "comprising" components A, B, and C may consist of (that is, contain only) components A, B, and C; or the article may contain not only components A, B, and C, but also one or more additional components.

As used herein, the term "derived" means obtained from a source, directly or indirectly. For example, cells may be directly derived from an organism by obtaining a tissue or organ from the organism, then disaggregating the tissue or organ to obtain primary cells. Cells may be obtained indirectly from an organism by, for example but not limited to, obtaining an isolate, typically a single cell isolate from a cell line that was obtained from the organism, then expanding the isolate to obtain a cell line comprising a multiplicity of cells, sometimes referred to as a subclone.

The term "lepidopteran insect" refers to any member of a large order (Lepidoptera) of insects comprising the butterflies, moths, and skippers that as adults have four broad or lanceolate wings usually covered with minute overlapping and often brightly colored scales and that as larvae are caterpillars. Exemplary lepidopteran insects include but are not limited to, *Spodoptera frugiperda, Bombyx mori, Heliothis subflexa,* and *Trichoplusia ni.*

As used herein, the term "substantially" refers to a variation of no more than plus or minus ten percent relative to the named item or items. For example but not limited to, a cell line that has an average cell diameter that is between 90% and 110% of the average diameter of Sf9 cells, based on a statistically significant sample size, when the cell line and the Sf9 cells are propagated under the same conditions, and the average cell diameter is determined as described herein; or a cell line that has a cell density that is between 90% and 110% of the cell density of Sf9 cells, based on a statistically significant sample size, when the cell line and the Sf9 cells are propagated under the same conditions, and the cell density is determined as described herein.

The terms "testing for the presence of virus", "testing for the presence of Sf-rhabdovirus", "testing for the presence of Tn-nodavirus", "detecting the presence or absence of virus" and related terminology are used in a broad sense herein. Those in the art understand there are numerous testing techniques known in the art that may be employed in the context of the current teachings. Exemplary techniques suitable for testing for the presence of virus include, Reverse Transcription (RT), RT-Polymerase Chain Reaction (RT-PCR), RT-PCR coupled with nested PCR (for example but not limited to the exemplary techniques disclosed in Examples 4, 16, and 22), quantitative PCR (sometimes referred to as real-time PCR), various probe hybridization techniques, electron microscopy, and various antibody-based detection techniques known in the art, for example but not limited to an ELISA assay comprising at least one anti-virus antibody. In the case of a virus that is lytic or causes observable cytopathic effect (CPE) in the cell, exemplary testing techniques include without limitation, plaque assay and observation of CPE, which may comprise the use of microscopy. Bioinformatics techniques, for example but not limited to BLAST searching electronic databases of RNA or DNA sequences contained in cell lines or organisms of interest, are also within the scope of the current teachings.

According to certain embodiments, an established cell line characterized by a lack of virus is derived from an organism that is infected with a virus, for example but not limited to a virus-free established cell line derived from a virus-contaminated organism. In certain embodiments, the cell line is derived from an insect contaminated with a virus. In certain embodiments, the insect comprises a lepidopteran insect, for example but not limited to, *Spodoptera frugiperda* (Sf), *Bombyx mori, Heliothis subflexa,* or *Trichoplusia ni.* In certain embodiments, the cell line is derived from an Sf cell line, for example but not limited to, the Sf9 or Sf-21 cell lines. In certain embodiments, the cell line is derived from *Trichoplusia ni* contaminated with a virus or a virus-contaminated *Trichoplusia ni* cell line, for example but not limited to, the TN-368 cell line contaminated with an alphanodavirus.

In certain embodiments, an established cell line is characterized by having the same or substantially the same cell density, doubling time, average cell diameter, morphology, and N-glycosylation pattern as the virus-contaminated cells from which the cell line was derived, when: (1) the virus-free and virus infected cell lines are propagated under the same conditions, (2) the comparison is performed as described herein, and (3) the comparisons are based on a statistically significant sample size. In certain embodiments, cell lines are characterized by the production of more infectious recombinant baculovirus than the virus-infected cells from which the cell line was derived, when each are infected with AcP(−)p6.9hEPO or AcP(−)p6.9hSEAP under the same conditions and the comparison is performed according to Example 11. In certain embodiments, cell lines of the current teachings are susceptible to Sf-rhabdovirus infection.

According to certain exemplary methods for obtaining cell lines that lack virus, one or a few cells are isolated from a population of cells that are infected with virus, such as a cell line that is contaminated with a virus or cells from a disaggregated tissue or organ or from an organism that is infected with a virus. The isolated cell or cells are combined with an appropriate cell culture media that contains one or more antiviral compound to form a first culture composition. This first culture composition is incubated under conditions suitable for the cells to grow and divide; and for a sufficient period of time to allow the one or more antiviral compounds to affect viral replication. In certain method embodiments, an aliquot of the cells or culture media are removed from the culture and tested for the presence of virus. Cells lacking virus are combined with culture media that does not contain an antiviral compound to form a second culture composition. This second culture composition is incubated under conditions to allow the cells to grow and divide. The cells are expanded to obtain a cell line that lacks the virus that contaminated the organism or the cells from which the cell line was obtained.

In certain embodiments, methods for obtaining a virus-free cell line comprise: isolating a single cell from a population of lepidopteran insect cells, for example but not limited to, *Spodoptera frugiperda* or *Trichoplusia ni*cells; combining the isolated cell with cell culture media comprising at least one antiviral compound to form a first culture composition; incubating the first culture composition under conditions suitable for the cell to grow and divide, thereby generating a multiplicity of cells; optionally, removing a portion of the cells or the cell culture media and testing for the presence of Sf-rhabdovirus or a nodavirus; combining at least some of the multiplicity of cells from the first culture composition with cell culture media without an antiviral compound to form a second culture composition; and incubating the second culture composition under conditions suitable for the cells to grow and divide, thereby obtaining a cell line characterized by a lack of virus.

According to certain method embodiments, established cell lines that lack virus, for example but not limited to, Sf-rhabdovirus or Tn-nodavirus, are obtained. In certain method embodiments, an individual cell or small groups of cells, for example but not limited to, groups of 2 cells, 3 cells, 4 cells, 5 cells, 10 or fewer cells, or 20 or fewer cells (including every whole number between 1 and 20) are isolated from a population of cells that is infected with a virus. Non-limiting examples of techniques for isolating a single cell or small numbers of cells include limiting dilution cloning (sometimes referred to as cloning by serial dilution), cloning cells in soft agar and subsequently picking cell colonies, cell sorting to isolate single or small numbers of cells, laser capture microdissection (LCM), using micropipettes (for example but not limited to ultra-thin capillaries) to manually capture individual or small numbers of cells, microfluidics, or using micromanipulators to microscopically assist the selection of single or small numbers of cells. In certain embodiments, isolating a single cell comprises limited dilution cloning.

In certain method embodiments, isolated single cells or small groups of cells are combined with cell culture media comprising at least one antiviral compound to form a first culture composition. Exemplary antiviral compounds include but not limited to, drugs such as nucleoside analogs, interferon, and viral-specific antibodies, for example but not limited to neutralizing monoclonal or polyclonal antibodies. Non-limiting examples of nucleoside analogs include ribavirin, 6-azauridine, vidarabine, acyclovir, 9-/3-D-Arabino-furanosyladenine (Ara-A), cytosine arabinose, adenine arabinoside, and Guanine 7-N-oxide (G-7-Ox). In certain method embodiments the at least one antiviral compound comprises 6-azauridine. In certain embodiments, the antiviral compound is selected from ribavirin, 6-azauridine, vidarabine, acyclovir, 9-/3-D-Arabinofuranosyladenine (Ara-A), cytosine arabinose, adenine arabinoside, and Guanine 7-N-oxide (G-7-Ox). In certain embodiments, the antiviral compound is 6-azauridine. In certain embodiments, the antiviral compound comprises ribavirin.

According to certain method embodiments, the first culture composition is incubated under conditions suitable for cell growth. According to certain disclosed methods, cells or cell culture supernatant obtained from the first culture composition are tested for the presence or absence of virus, for example but not limited to, RT-PCR, nested PCR, or RT-PCR and nested PCR, followed by analysis of resulting amplicons for the presence or absence of virus specific amplification products. In certain method embodiments, the presence or absence of infectious virus is determined by: (1) combining (a) potentially infected cells or cell culture supernatant in which the potentially infected cells were incubated with (b) cells that are susceptible to infection by the potential virus (c) in a suitable cell culture media; (2) incubating this culture under conditions suitable for the virus to infect the cells; and (3) monitoring the cultured cells or the media in which they have been cultured for the presence of viral nucleic acid. In certain embodiments, the cells or culture media is periodically tested for the presence of virus, for example but not limited to, by using a virus-specific RT-PCR followed by nested PCR, then determining the presence or absence of specific amplicons.

According to certain embodiments, after the isolated cells have been incubated in the first culture composition for a suitable period to inhibit viral replication and samples of the corresponding cells or culture media have been tested and found not to contain virus, the cells are combined with cell culture media that does not contain an antiviral compound to form a second culture composition. The second culture composition is incubated under suitable conditions for cell growth. In certain embodiments, the cells or culture media from the second culture composition are tested for the presence or absence of virus.

Those in the art will appreciate that conditions suitable for growing a particular cell type are readily ascertainable from a variety of sources, for example but not limited to, cell culture manuals, commercial cell banks, or vendors of culture media and/or plastic ware. Appropriate cell culture conditions may also easily determined using methods known in the art.

In certain embodiments, cell lines are derived from primary cells that are contaminated with virus, for example but not limited to Sf-rhabdovirus or Tn-nodavirus. In certain embodiments, cell lines are derived from a cell line that is infected with virus, including but not limited to Sf-rhabdovirus or Tn-nodavirus. In certain embodiments, the population of infected cells are part of an infected cell line. In certain embodiments, the infected cell line was obtained from an infected organism, for example but not limited to, moths, caterpillars, or other insects that are persistently infected with a virus. In certain embodiments, the cell line is derived from a contaminated cell line that was derived from an insect infected with virus, for example but not limited to Sf cell lines infected with Sf-rhabdovirus. In certain embodiments, the cell line is a *Trichoplusia ni* cell line contaminated with Tn-nodavirus, for example but not limited to TN-368, BTI-Tn-561-4 (also known as HIGH FIVE™), or Tni PRO cells.

According to certain disclosed methods, the cells or cell culture media in which the cells were grown is tested for the presence or absence of virus. In certain methods, the testing comprises RT-PCR and nested PCR; quantitative PCR; probe hybridization techniques; bioinformatics methods including but not limited to BLAST searching; plaque assay, CPE observation, or antibody-based detection methods.

CERTAIN EXEMPLARY EMBODIMENTS

Example 1. Insect cell culture. Sf9 cells, known to be contaminated with Sf-rhabdovirus, were routinely maintained as shake-flask cultures at 28° C. in ESF 921 medium (Expression Systems, Woodland, Calif.). TN-368 cells, known to be contaminated with Tn-nodavirus, were routinely maintained as adherent cultures at 28° C. in TN-MFH medium supplemented with 10% fetal bovine serum (Atlanta Biologicals, Inc., Flowery Branch, Ga.) and 1% pluronic F-68 (Invitrogen, Carlsbad, Calif.).

Figure 1B:
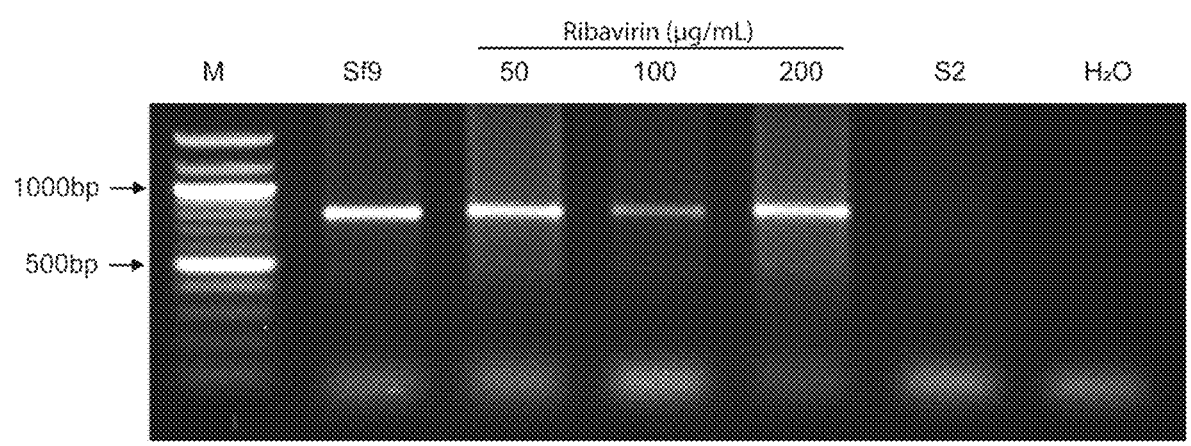
Figure 1C:
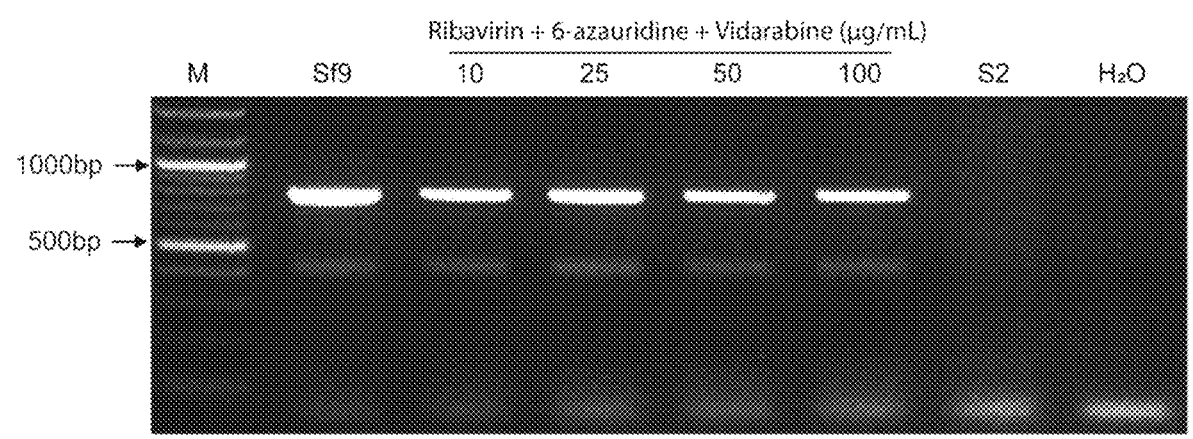
Figure 2A:
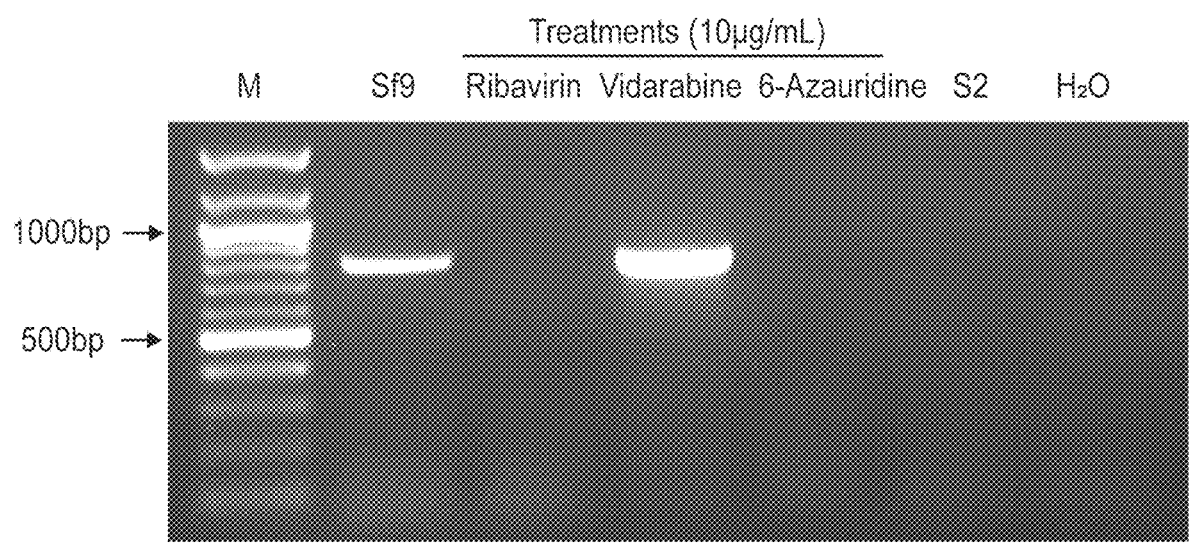
FIGS. 2A-2B: Sf-rhabdovirus in isolated antiviral drug-treated Sf9 cell subclones. Single Sf9 cell subclones were isolated by limiting dilution and treated for about a month with various antiviral drugs, and then total RNA was extracted from individual clones and tested for Sf-rhabdovirus RNA by RT-PCR (FIG. 2A) or RT-PCR, followed by nested PCR (FIG. 2B), as described in Example 4. All results shown in FIGS. 2A-2B were obtained using RNA from cells that were still being cultivated in the presence of antiviral drugs. The positive and negative controls and 100-bp markers were as described in the brief description of FIGS. 1A-1C.
Figure 2B:
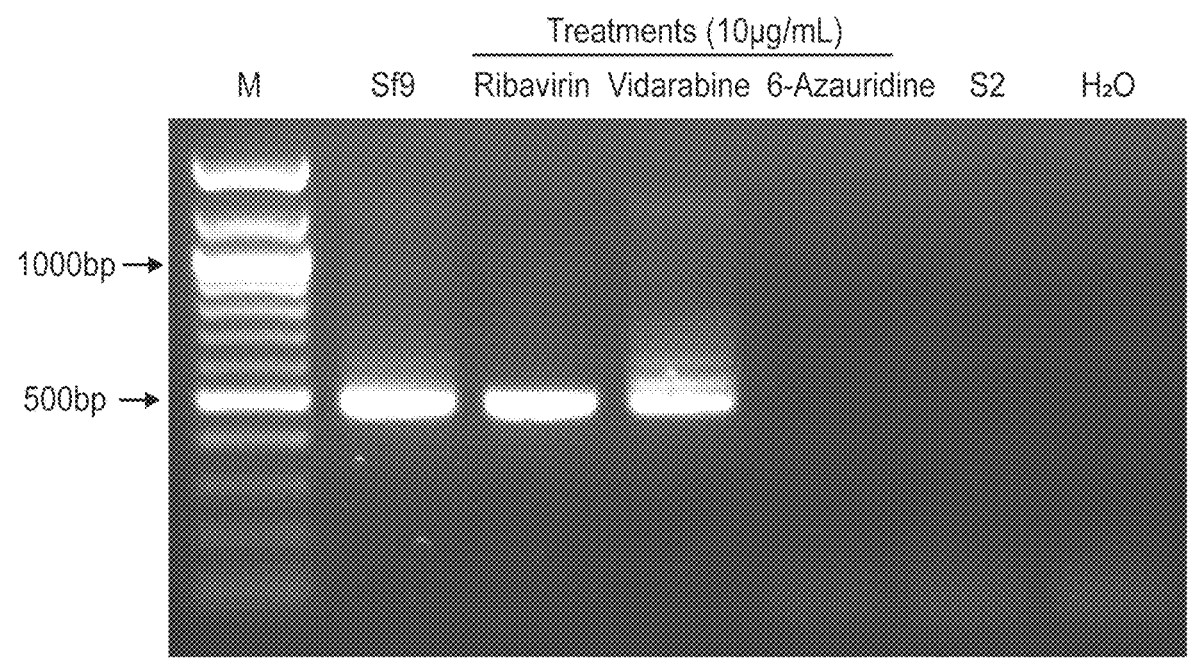

Example 2. Conventional methodology fails to produce an established *S. frugiperda* cell line that lacks virus. Our initial efforts to isolate an Sf-rhabdovirus-free derivative involved culturing polyclonal Sf9 cell populations in TNM-FH medium supplemented with 10% (v/v) fetal bovine serum (Atlanta Biologicals, Inc., Flowery Branch, Ga.) plus various concentrations of ribavirin (Oxchem Corporation, Irwindale, Calif.). Subsequently, we treated polyclonal Sf9 cell populations with various concentrations of three antiviral drugs, ribavirin, 6-azauridine (Alfa Aesar, Ward Hill, Mass.) and vidarabine (TCI America, Portland, Oreg.). The Sf9 cells were cultured with these three drugs for about a month with ad hoc serial passages and samples were routinely tested for Sf-rhabdovirus contamination by RT-PCR, as described in Example 4. After about a month of treatment with 100 µg/ml of ribavirin, we obtained a Sf9 subclone containing no RT-PCR-detectable Sf-rhabdovirus (FIG. 1A). This Sf-rhabdovirus-free subclone was transferred to TNM-FH medium supplemented with 10% (v/v) fetal bovine serum, but no antiviral drugs, and re-tested by RT-PCR/nested PCR, as described in Example 4. To our surprise, when these cells were transferred to a culture medium lacking antiviral drugs, they reverted to the Sf-rhabdovirus-positive phenotype (FIG. 1B). We subsequently treated polyclonal Sf9 cell populations with various concentrations of a combination of three antiviral drugs, ribavirin, 6-azauridine, and vidarabine. Again, we were surprised to find cells treated with these three drugs for about a month were still positive for Sf-rhabdovirus (FIG. 1C). Thus, in stark contrast to previous work, in which vertebrate cells were cured of rhabdoviral contamination by treatment with these same antiviral drugs, this approach failed to eliminate Sf-rhabdovirus from Sf9 cells Example 3. Exemplary method for obtaining an established Sf cell line characterized by a lack of virus. After discovering polyclonal Sf9 cell cultures treated with antiviral drugs reverted to the Sf-rhabdovirus-positive phenotype when grown in drug-free media, we developed novel methods for obtaining established virus-free cell lines derived from virus-contaminated starting material. This exemplary embodiment comprised isolating single Sf9 cells by limiting dilution, then treating the isolated cell subclones with antiviral drugs. The cells were seeded into 96-well plates in TNM-FH medium supplemented with 10% (v/v) fetal bovine serum (Atlanta Biologicals, Inc., Flowery Branch, Ga.) plus 10 µg/ml of ribavirin (Oxchem Corporation, Irwindale, Calif.), 6-azauridine (Alfa Aesar, Ward Hill, Mass.), or vidarabine (TCI America, Portland, Oreg.). The cells were cultured for about a month with ad hoc amplification to produce progressively larger cultures and, after achieving the 25 cm$^2$ flask level, samples were tested for Sf-rhabdovirus contamination by PCR, as described in Example 4. A clone lacking Sf-rhabdovirus contamination (FIG. 2B) was transferred to media lacking antiviral drugs, designated Sf-RVN passage zero (PO) and, at P2, transferred to a shake-flask culture in serum-free ESF 921 medium and subsequently maintained in this culture medium and format.

Example 4. Sf-rhabdovirus-specific Reverse Transcription-PCR (RT-PCR)/nested PCR. Samples of Sf9 and Sf-RVN cultures containing 1×10$^6$ cells were harvested and the cells were pelleted by low speed centrifugation. The cell-free supernatants were filtered through a 0.22 µm filter (CELLTREAT Scientific, Shirley, Mass.) and then ultracentrifuged at 131,000×g for 22 h at 4° C. Total RNA was extracted from both the low speed cell and high speed cell-free pellets using the RNASo/v reagent (Omega Bio-Tek, Inc., Norcross, Ga.), according to the manufacturer's protocol. The RNAs were then quantified and used as templates for cDNA synthesis with the ProtoScript II First Strand cDNA synthesis kit (New England Biolabs, Ipswich, Mass.) and an Sf-rhabdovirus-specific primer designated 320-SP1 (SEQ ID NO: 9), according to the manufacturer's protocol. Equivalent amounts of each cDNA preparation were used for PCR's with Taq DNA polymerase, ThermoPol reaction buffer (New England Biolabs), and Sf-rhabdovirus-specific primers Mono-1 (SEQ ID NO: 1) and Mono-2 (SEQ ID NO: 2). The reaction mixtures were incubated at 94° C. for 3 min, cycled 35 times at 94° C. for 30 s, 55° C. for 1 min, and 72° C. for 1 min, and finally incubated at 72° C. for 10 min. One µL of each primary PCR (RT-PCR) was then used as the template for secondary PCR's (RT-PCR/nested PCR) under the same conditions, except the primers were nested Sf-rhabdovirus-specific primers Mono-1i (SEQ ID NO: 7) and Mono-2i (SEQ ID NO: 8). The RT-PCR and RT-PCR followed by nested PCR products were analyzed by agarose gel electrophoresis with ethidium bromide staining according to standard methodology. The sequence of each primer used for these assays is shown in Table 1.

TABLE 1

Sf-rhabdovirus-specific primers

| Primer | Sequence (5' to 3') | Product size (bp)[1] |
|---|---|---|
| Mono-1 | GGCAAGGCTGTTTGGATTACTGACC (SEQ ID NO: 1) | |
| Mono-2 | ACAGGTTTGCAGCTAAGGAGGACA (SEQ ID NO: 2) | 794 |
| Mono-3 | TGGCGAGGGACTGCTTACAGAAGG (SEQ ID NO: 3) | |
| Mono-4 | CACAGCCGGGGTGCAATCA (SEQ ID NO: 4) | 730 |
| Mono-5 | ACAGGAGATGCGGAAGACCCCTC (SEQ ID NO: 5) | |
| Mono-6 | ATCTCGCAGGTGGGACAACCCC (SEQ ID NO: 6) | 826 |
| Mono-1i | ATATGAGAGCCCCAGACACACAGCC (SEQ ID NO: 7) | |
| Mono-2i | ACGATGTGGTGAGAGAAACACCTCCT (SEQ ID NO: 8) | 501 |
| 320-SP1 | CACATCTAGAGCTTGAAGACC (SEQ ID NO: 9) | |
| 320-ASP1 | ACCATCACAGCCAGTGCTG (SEQ ID NO: 10) | 481 |

[1]Size of the amplification products resulting from PCR with odd/even primer pairs (e.g., Mono-1 and Mono-2; or 320-SP1 and 320-ASP1).

Figure 3A:
FIGS. 3A-3C: Absence of Sf-rhabdovirus in Sf-RVN cells. Total RNA was isolated from an exemplary cell line, referred to as "Sf-RVN", at various passage levels and assayed for the presence of Sf-rhabdovirus using the Sf-rhabdovirus-specific RT-PCR, followed by nested PCR, as described in Example 4. This exemplary cell line was generated by expanding a 6-azauridine-treated Sf9 subclone found to be negative for Sf-rhabdovirus contamination in FIG. 2B. The Sf-rhabdovirus-specific RT-PCR/nested PCR results demonstrated that no Sf-rhabdovirus was present over the course of 60 passages and 120 passages of the Sf-RVN cells (FIGS. 3A and 3B, respectively). We also isolated total RNA from the pellet fraction obtained by ultracentrifuging the cell-free media (CFM) from Sf-RVN cells at passage 60. The total RNA from this CFM pellet was assayed for Sf-rhabdovirus using the Sf-rhabdovirus-specific RT-PCR/nested PCR.
Figure 3B:
Figure 3C:
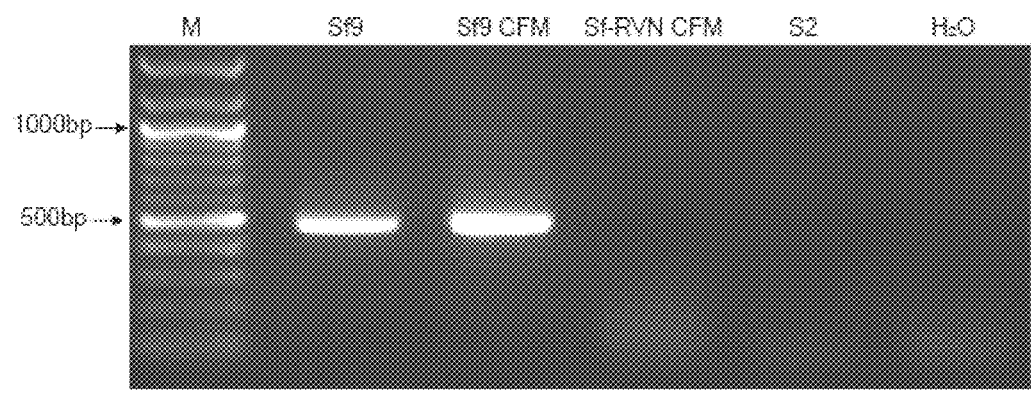

Example 5. Exemplary Sf subclone "Sf-RVN" lacks Sf-rhabdovirus. Total RNA was isolated from Sf-RVN cell extracts at various passage levels and tested for the presence of Sf-rhabdovirus using RT-PCR/nested PCR, as described in Example 4. A strong amplification product of the expected size was observed when total RNA from Sf9 cells was used as a positive control for this assay, as expected (FIGS. 3A, 3B, and 3C). In contrast, no products were observed when we used total RNAs isolated from Sf-RVN cells every five passages during the course of either 60 (FIG. 3A) or 120 (FIG. 3B) sequential passages in the absence of any antiviral drugs our lab. We also observed no amplification products in negative controls with total RNA isolated from *D. melanogaster* S2R+ cells, which do not support Sf-rhabdovirus replication. We observed strong amplification products of the expected sizes when we used two other Sf-rhabdovirus-specific primer pairs (Mono-3 (SEQ ID NO: 3)/Mono-4 (SEQ ID NO: 4) and Mono-5 (SEQ ID NO: 5)/Mono-6 (SEQ ID NO: 6); see Table 1), which were derived from other regions of the I-protein coding sequence of Sf-rhabdovirus, for RT-PCRs with total RNA isolated from Sf9 cells, but not from Sf-RVN cells (data not shown). Finally, we observed a strong amplification product of the expected size in RT-PCR/nested PCR assays with total RNA isolated from pellets obtained by ultracentrifuging Sf9 cell-free media, but not Sf-RVN cell-free media, when tested after 60 passages (FIG. 3C). Together, these results demonstrated there was no detectable Sf-rhabdovirus RNA in Sf-RVN cells or cell-free media over the course of 120 passages in the absence of any antiviral drugs, which indicates these cells are Sf-rhabdovirus-free.

Figure 4:
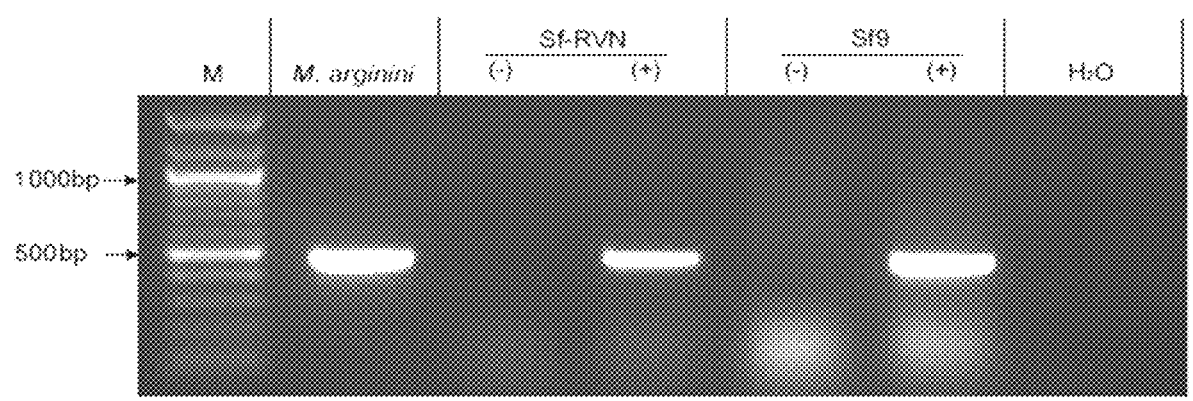
FIG. 4: *Mycoplasma* assays. Sf-RVN and Sf9 cell extracts (−) were assayed for *mycoplasma* contamination using the PCR-based Universal *Mycoplasma* Detection Kit (American Type Culture Collection), as described in Example 6. A plasmid encoding an *M. arginini* rRNA target sequence was used as the positive control (FIG. 4, lane "*M. arginini*"). Additional controls were performed using Sf-RVN and Sf9 cell lysates spiked with this plasmid (FIG. 4, lanes marked Sf-RVN (+) and Sf9 (+), respectively) to determine if the lysate interfered with the assay. A negative control reaction was performed with no template (FIG. 4, lane H2O). The lane marked M shows the 100-bp markers, with selected sizes indicated on the left.

Example 6. *Mycoplasma* detection. We also tested samples containing about $10^5$ Sf-RVN or Sf9 cells for *Mycoplasma* using the Universal *Mycoplasma* Detection kit from American Type Culture Collection (Manassas, Va.), according to the manufacturer's protocol. This PCR-based assay uses primers complementary to sequences conserved in the 16S rRNA genes of over 60 different *Mycoplasma, Acholeplasma, Spiroplasma* and *Ureaplasma* species, including eight species that are frequently found as contaminants of cell cultures. The results shown in FIG. 4 demonstrated neither the Sf9 nor the Sf-RVN cells were detectably contaminated with *Mycoplasma*. The absence of a PCR product was not due to inhibition of the PCR reaction by the insect cell lysates, as amplicons of the expected sizes were observed in PCRs performed using lysates spiked with the control templates (FIG. 4).

Example 7. Cell growth properties, morphologies, and diameters. Sf-RVN or Sf9 cells were seeded at a starting density of $1.0 \times 10^6$ cells/ml in 50 ml shake flask cultures, triplicate samples were removed every 24 h for 4 days, and viable cell densities and sizes were measured using a COUNTESS® automated cell counter (ThermoFisher Scientific, Inc.). Doubling times were calculated using the formula: $Td = T \times Log\ 2/Log(Q2/Q1)$ where Td=doubling time, T=time (h) elapsed since the last passage, O1=cell seeding density, and O2=viable cell count. Cell morphologies were documented by collecting phase contrast images at a magnification of 10× using an Olympus FSX-100 microscope and FSX-BSW imaging software (Olympus Life Sciences Solutions, Center Valley, Pa.).

Figure 5A:
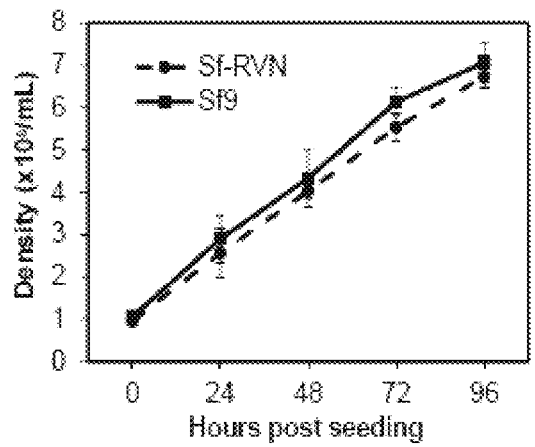
FIGS. 5A-5D: *Spodoptera* cell growth and morphology. Sf-RVN and Sf9 cells were seeded into shake flasks at a density of $1.0 \times 10^6$ cells/ml in ESF 921 medium. Triplicate samples were harvested at various times after seeding and viable cell counts and diameters were measured with an automated cell counter, as described in Example 7. The figure shows the average viable cell densities (FIG. 5A), diameters (FIG. 5B), and doubling times (FIG. 5C) measured in three independent experiments, as well as phase contrast micrographs of Sf-RVN and Sf9 cells at a magnification of 10× FIG. 5D). The error bars represent the confidence intervals ($P<0.05$).
Figure 5B:
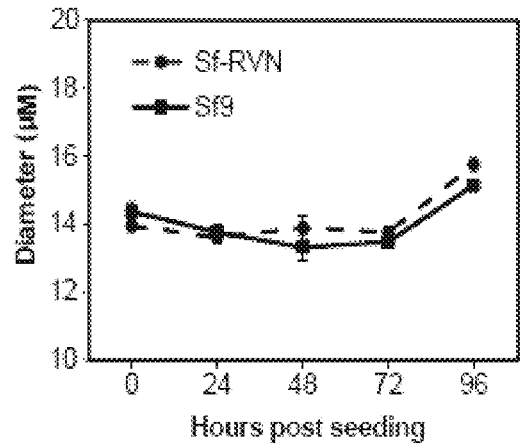
Figure 5C:
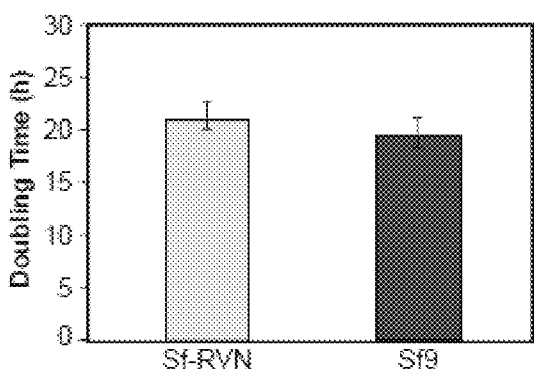
Figure 5D:
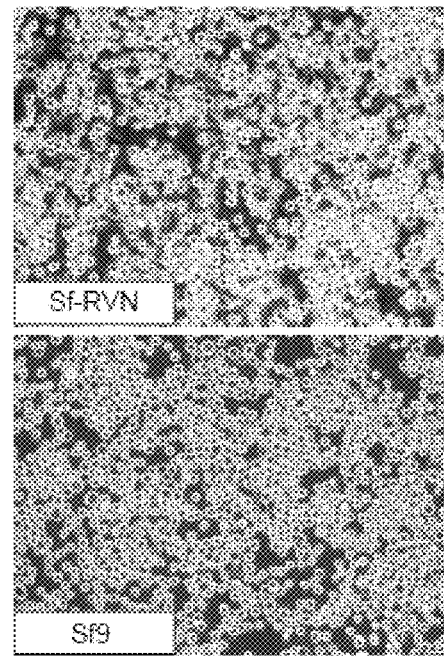

To compare several general properties of Sf-RVN cells to those of Sf9, we evaluated their culture densities, diameters, doubling times, morphologies, and viabilities in response to baculovirus infection. The results showed that Sf-RVN and Sf9 cells achieved virtually identical average densities over the course of four days after being seeded into parallel shake flask cultures in ESF-921 medium (FIG. 5A). This time frame encompassed the 2-3 days of growth typically allowed between serial passages during routine insect cell line maintenance. The results also revealed no significant differences in the average diameters (FIG. 5B), doubling times (FIG. 5C), or morphologies (FIG. 5D) of Sf-RVN and Sf9 cells during the course of these cell culture experiments. Finally, we found no significant differences in the viabilities of Sf-RVN and Sf9 cells in response to baculovirus infection, which were indistinguishable over 4 days after infection at multiplicities of either 0.1 (FIG. 6A) or 5 (FIG. 6B) pfu/cell. The time frame and two different MOIs used in this experiment encompassed the conditions typically used to produce either baculovirus working stocks or recombinant proteins at low or high MOIs, respectively. Overall, the results of these experiments demonstrated that the general properties of Sf-RVN and Sf9 cells examined in this study are indistinguishable.

Example 8. Baculovirus expression vectors. A baculovirus expression vector designated BacPAK6-h.Chi/Cath encoding full-length, untagged *E. coli* 13-galactosidase (B-gal) was produced in two sequential steps. In the first step, BacPAK6 viral DNA was recombined with a plasmid encoding *E. coli* B-glucuronidase under the control of the baculovirus p6.9 promoter. In this plasmid, the p6.9-B-glucuronidase gene was inserted in place of the AcMNPV chiA and v-cath genes and embedded within wild type AcMNPV flanking sequences. The desired recombinant was tentatively identified by its blue plaque phenotype in the presence of X-GlcA (RPI Corp., Mount Prospect, Ill.). The recombination site was confirmed by PCR with primers specific for the B-glucuronidase gene and 5' UTR of the AcMNPV gp64 gene, which were internal and external to the transfer plasmid, respectively. This virus was amplified and viral DNA was isolated and digested with I-SeeI to delete the entire B-glucuronidase expression cassette. In the second step, Sf9 cells were transfected with the I-SeeI-digested viral DNA. The resulting progeny were resolved by plaque assay in the presence of X-GlcA and the final recombinant baculovirus, BacPAK6-L1Chi/Cath, was identified by its white plaque phenotype.

The recombinant baculovirus expression vectors designated AcP(−)p6.9hSEAP and AcP(−)p6.9hEPO encoded 8× HIS-tagged (SEQ ID NO: 27) forms of human secreted alkaline phosphatase (hSEAP) and human erythropoietin (hEPO), respectively, under the control of AcMNPV p6.9 promoters and honeybee prepromellitin signal peptides. Synthetic genes encoding mature SEAP and EPO (Genbank NP_001623.3 amino acids 23-511 and Genbank NP_000790.2 amino acids 28-193, respectively) with N-terminal TEV protease cleavage sites (ENLYFQG (SEQ ID NO.: 28)) were designed using OPTIMIZER (Puigbo et al., 2007) to match AcMNPV codon usage (www.kazusa.or.jp). These sequences were synthesized, cloned, and sequenced by Genscript (Piscataway, N.J.) and error-free clones were used to produce recombinant baculovirus expression vectors by in vitro recombination with Ac6.9GT, as described previously (Toth et al., 2011).

Standard methods were used to plaque-purify, amplify, and titer recombinant baculovirus expression vectors in Sf9 cells. In addition, Sf-rhabdovirus and Tn-nodavirus-free stocks were produced for this study. First, Sf9 cells were infected with working stocks of each baculovirus vector, and then baculoviral DNA was isolated using a standard method. This method includes proteinase K, SOS, and RNaseA treatments, followed by phenol/chloroform/isoamyl alcohol extraction and DNA precipitation with isopropanol, which was expected to eliminate Sf-rhabdovirus and Tn-nodavirus. The resulting baculoviral DNA preparations were then used to transfect Sf-RVN cells and the progeny were plaque-purified, amplified, and titered, except Sf-RVN were used as the hosts for plaque-purification and amplification, instead of Sf9 cells. During this process, we tested the baculoviral DNA-transfected and baculovirus-infected Sf-RVN cell extracts, as well as the pellets obtained by ultracentrifuging samples of the final working virus stocks, for the presence or absence of Sf-rhabdovirus and Tn-nodavirus using the RT-PCR/nested PCR assays described in Examples 4. No Sf-rhabdovirus or Tn-nodavirus sequences were detected.

Example 9. Recombinant protein expression. Sf-RVN or Sf9 cells in ESF 921 culture media were seeded into six-well plates at densities of $1 \times 10^6$ cells/well. The cells were then mock-infected with ESF 921 media or infected with Sf-rhabdovirus-free stocks of BacPAK6-L1Chi/Cath, AcP(−) p6.9hSEAP, or AcP(−) p6.9hEPO at multiplicities of infection (MOIs) of either 0.1 or 5 plaque-forming units (pfu)/cell. At various times post infection, the infected cells were harvested, cell densities were measured, and the cells were pelleted by low speed centrifugation. The cells and cell-free media were then processed in various ways, depending upon the nature of the model protein being expressed and purpose of the experiment, as described below. In each case, however, the levels of recombinant protein in cell extracts and/or cell-free media were measured by sodium dodecyl sulfate polyacrylamide gel electrophoresis (SOS-PAGE; (Laemmli, 1970)) and immunoblotting (Towbin et al., 1979) with protein- or tag-specific primary antibodies and alkaline phosphatase-conjugated secondary antibodies, as specified below. Immunoreactive proteins were visualized using a standard alkaline phosphatase-based color reaction and relative intensities were estimated by scanning and quantitating the bands using Image J software version 1.48 (U.S. National Institutes of Health).

For B-gal, infected cell pellets were used to prepare cytoplasmic extracts for enzyme activity assays, using a known method. Immunoblotting was performed using rabbit anti-!3-gal (EMO Millipore Corporation, Germany) and alkaline phosphatase conjugated goat anti-rabbit IgG (Sigma-Aldrich, St. Louis, Mo.) as the primary and secondary probes, respectively.

For hSEAP, infected cell-free media were prepared for enzyme activity assays and immunoblotting was performed using mouse anti-penta-His (ThermoFisher) and alkaline phosphatase conjugated rabbit anti-mouse IgG (Sigma-Aldrich) as the primary and secondary probes, respectively.

For hEPO, infected cell-free media were prepared for immunoblotting with rabbit anti-hEPO (U-CyTech, Utrecht, The Netherlands) and alkaline phosphatase conjugated goat anti-rabbit IgG (Sigma-Aldrich) as the primary and secondary probes, respectively.

We compared the levels of baculovirus-mediated recombinant protein production supported by Sf-RVN and Sf9 cells, using E. coli B-gal, a model bacterial, intracellular protein; hSEAP, a model human, secreted glycoprotein; and hEPO, a model human, secreted glycoprotein of biotechnological significance. It is important to emphasize that Sf-rhabdovirus-free working stocks of each of the recombinant baculoviruses were prepared and used for these studies, as described above.

Figure 7A:
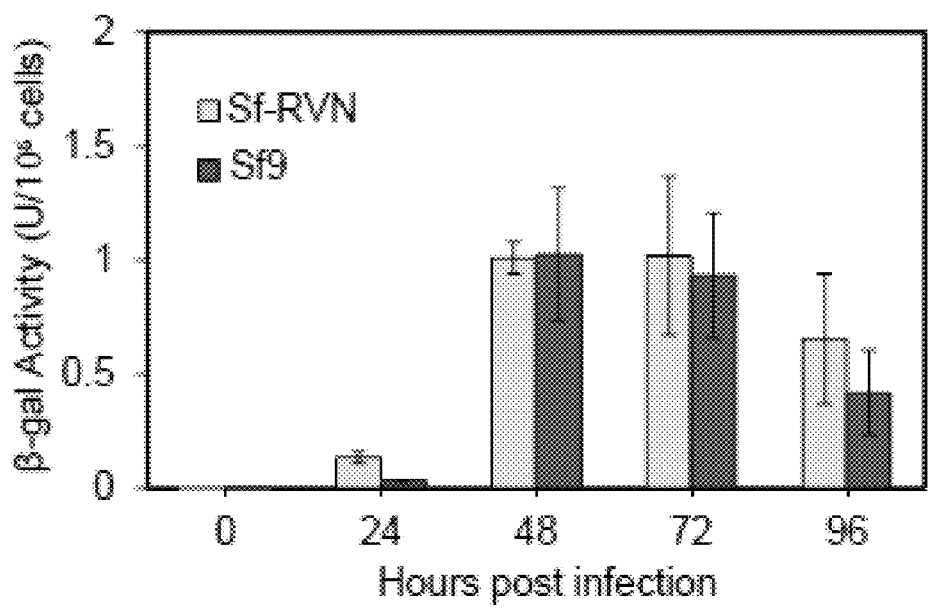
FIGS. 7A-7C: Recombinant B-gal production. Sf-RVN and Sf9 cells were infected with an Sf-rhabdovirus-free stock of BacPAK6-L1Chi/Cath at an MOI of 5 pfu/cell. Triplicate samples were harvested at various times post-infection and clarified intracellular extracts were assayed for) 13-gal activity (FIG. 7A), as described in Example 9. This plot shows the average results with error bars representing the confidence intervals ($P<0.05$). One set of extracts was also used to measure total intracellular B-gal production levels by immunoblotting analysis (FIG. 7B) with scanning laser densitometry (FIG. 7C) to estimate relative immunoreactive band densities. The same general trends were observed in two independent biological replicates of this experiment.
Figure 7B:
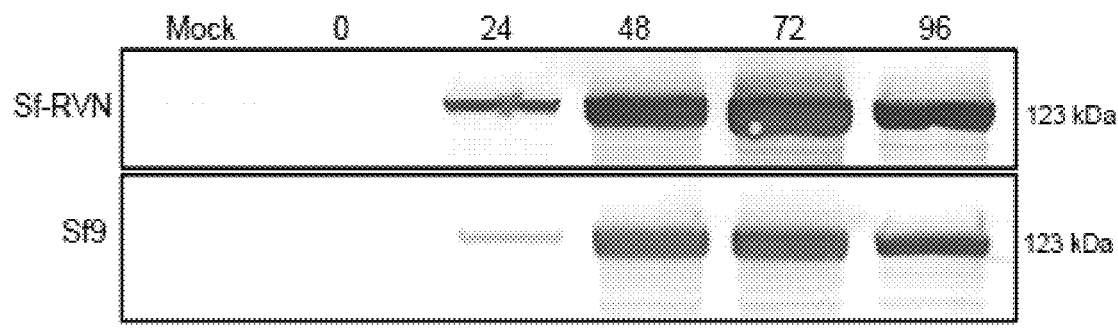
Figure 7C:
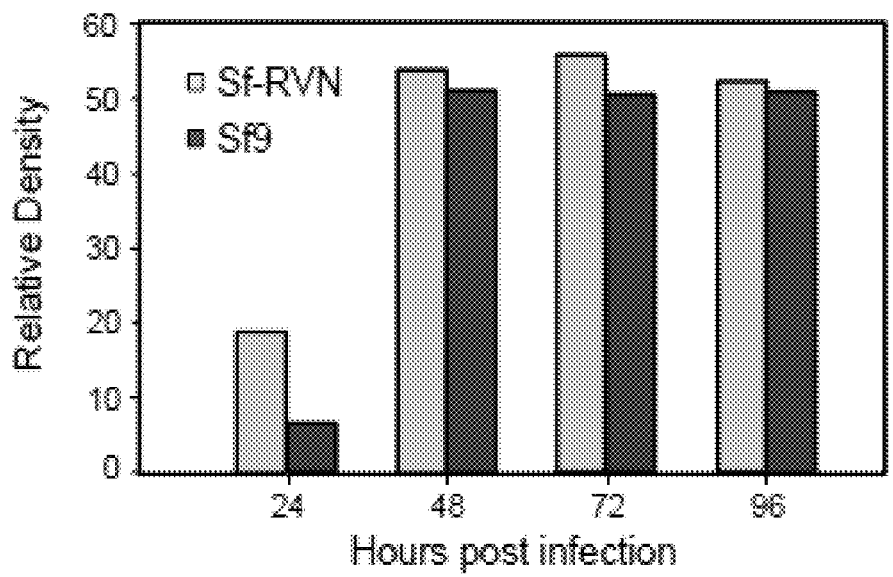

The E. coli B-gal expression experiments showed there were no significant differences in the intracellular enzyme activity levels produced by Sf-RVN and Sf9 cells during 4 days of infection with the recombinant baculovirus (FIG. 7A). Representative immunoblotting results, shown in FIG. 7B, indicated that Sf-RVN produced slightly more total intracellular B-gal protein. An independent biological replicate in which we stained the gel with Coomassie Brilliant blue yielded the same result, but as in the results shown in FIGS. 7A-7C, the increase in intracellular B-gal levels produced by Sf-RVN cells was minor (data not shown). Finally, we noted the levels of enzyme activity and immunoreactive intracellular B-gal produced by Sf-RVN and Sf9 cells were both lower at 4 days post-infection, as compared to earlier time points, which might reflect baculovirus-induced cytotoxicity at this very late time of infection.

Figure 6A:
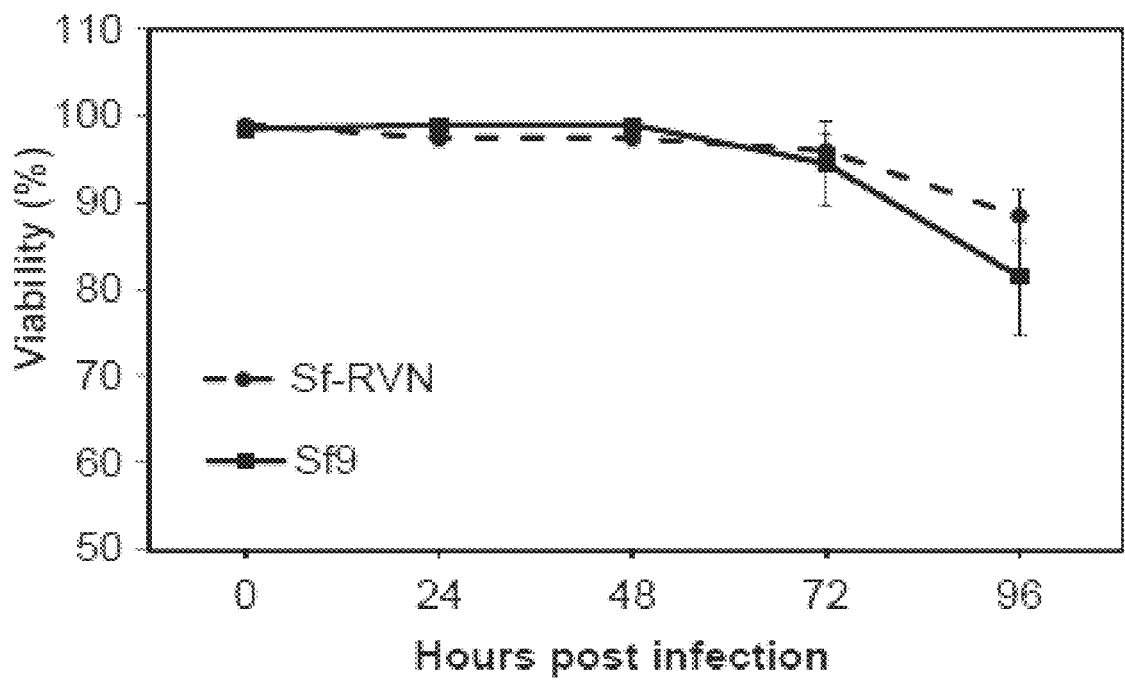
FIGS. 6A-6B: Cell viability after baculovirus infection. Sf-RVN and Sf9 cells were infected with an Sf-rhabdovirus-free stock of AcP(−)p6.9hSEAP at an MOI of 0.1 pfu/cell (FIG. 6A) or 5 pfu/cell (FIG. 6B). Triplicate samples were harvested at various times post-infection and viability was measured using an automated cell counter, as described in Example 7. The plots show the average percent viability measured in two independent experiments. The error bars represent the confidence intervals ($P<0.05$).
Figure 6B:
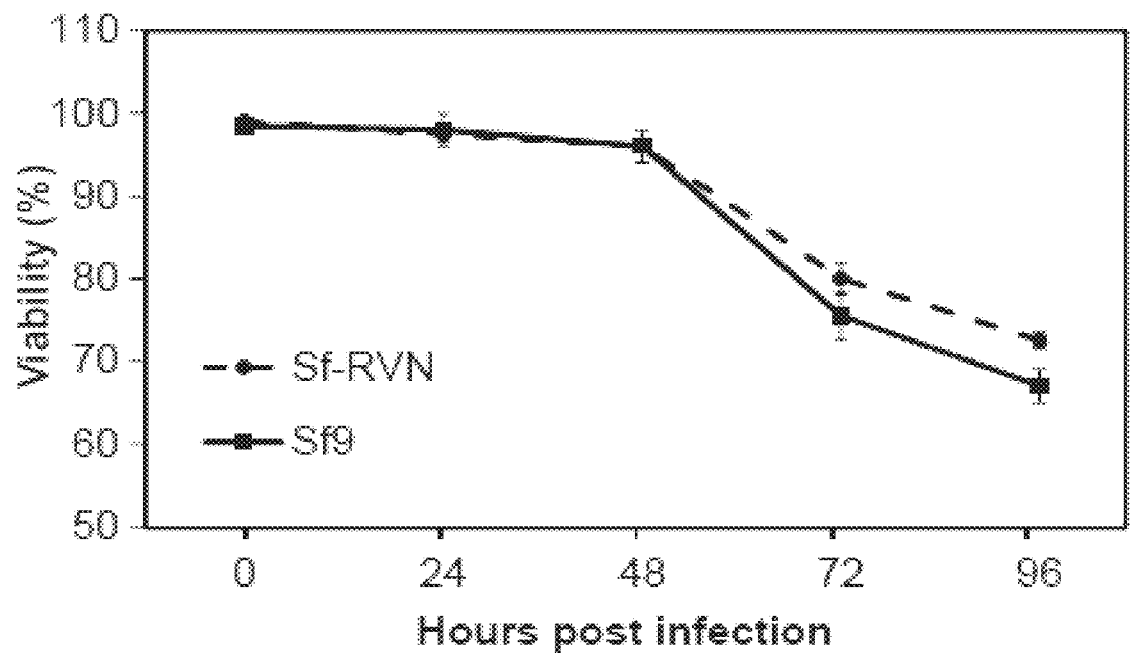
Figure 8A:
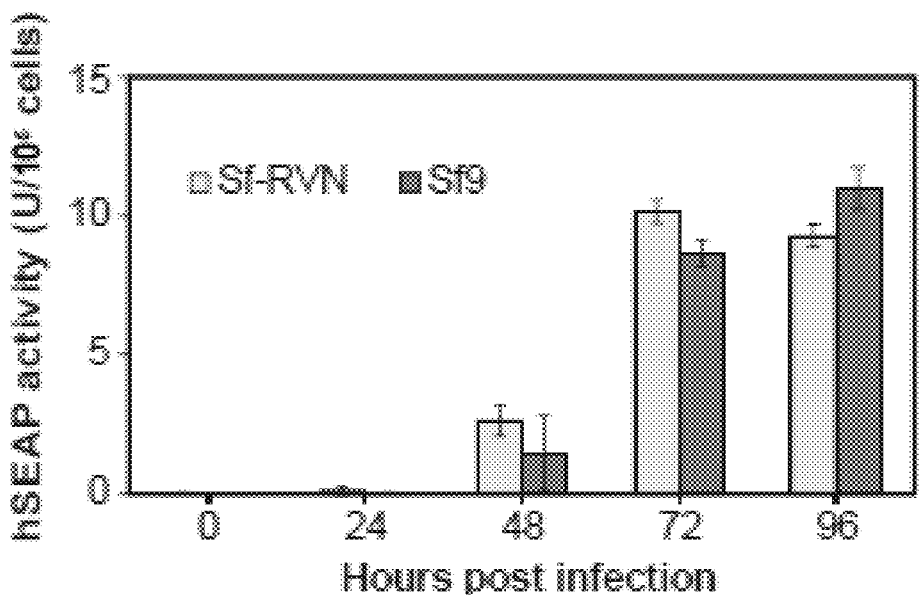
FIGS. 8A-8F: Recombinant hSEAP production. Sf-RVN and Sf9 cells were infected with an Sf-rhabdovirus-free stock of AcP(−)p6.9hSEAP at an MOI of 0.1 pfu/cell (FIGS. 8A, 8B, and SC) or 5 pfu/cell (FIGS. 8D, SE and SF). Triplicate samples were harvested at various times post-infection, cell-free media were prepared and assayed for hSEAP activity, as described in Example 9, and the average results were plotted with error bars representing the confidence intervals ($P<0.05$, FIGS. 8A and 8D). One set of cell-free media was also used to measure total extracellular hSEAP production levels by immunoblotting analysis (FIGS. 8B and SE) with scanning laser densitometry (FIGS. SC and SF) to estimate relative immunoreactive band densities.
Figure 8B:
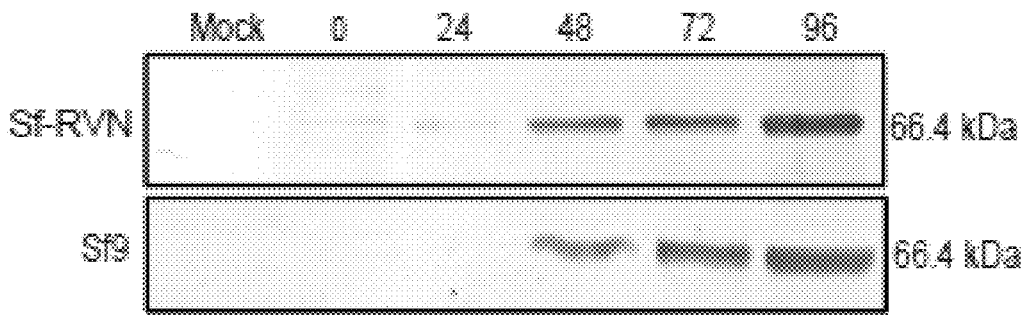
Figure 8C:
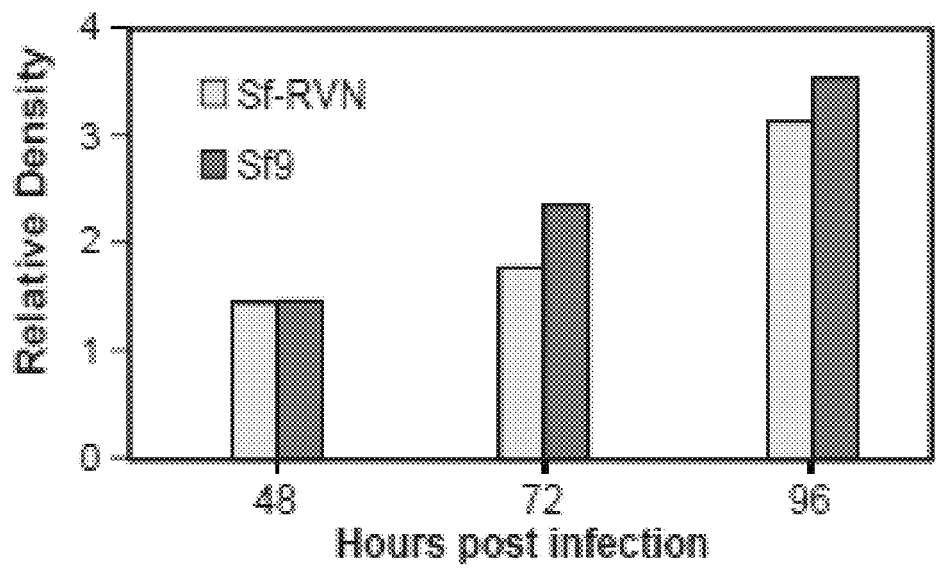
Figure 8D:
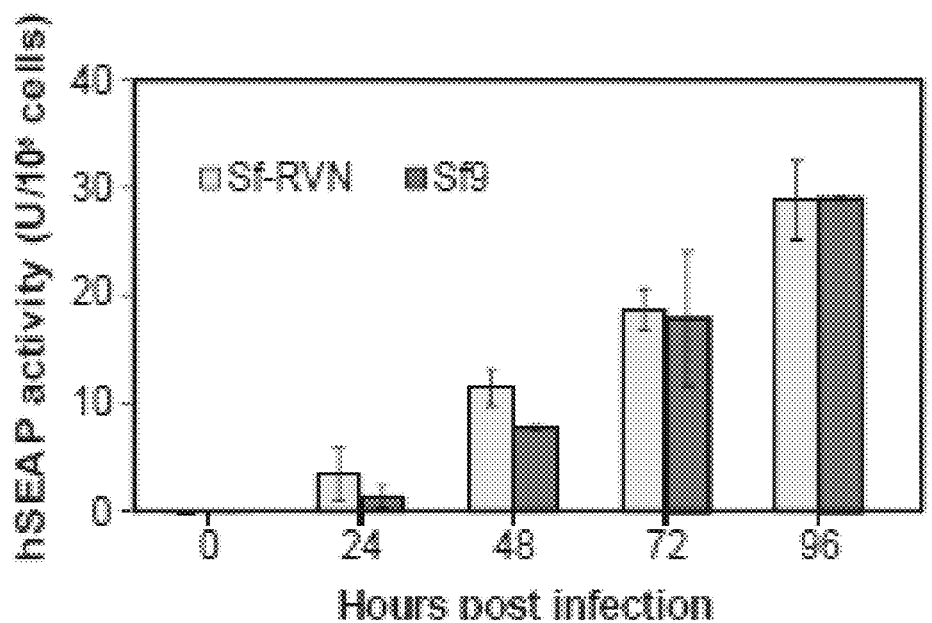
Figure 8E:
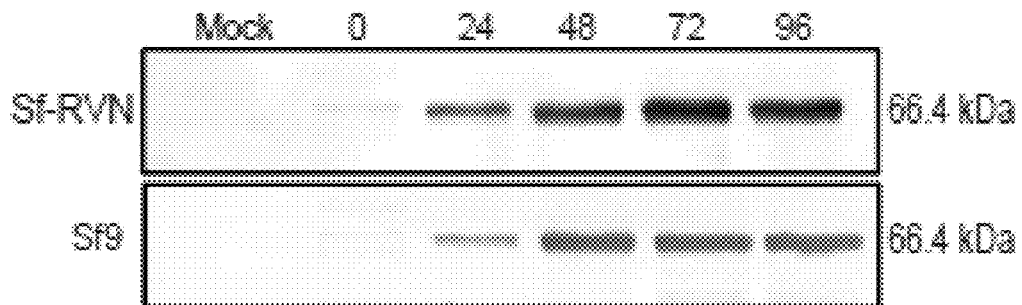
Figure 8F:
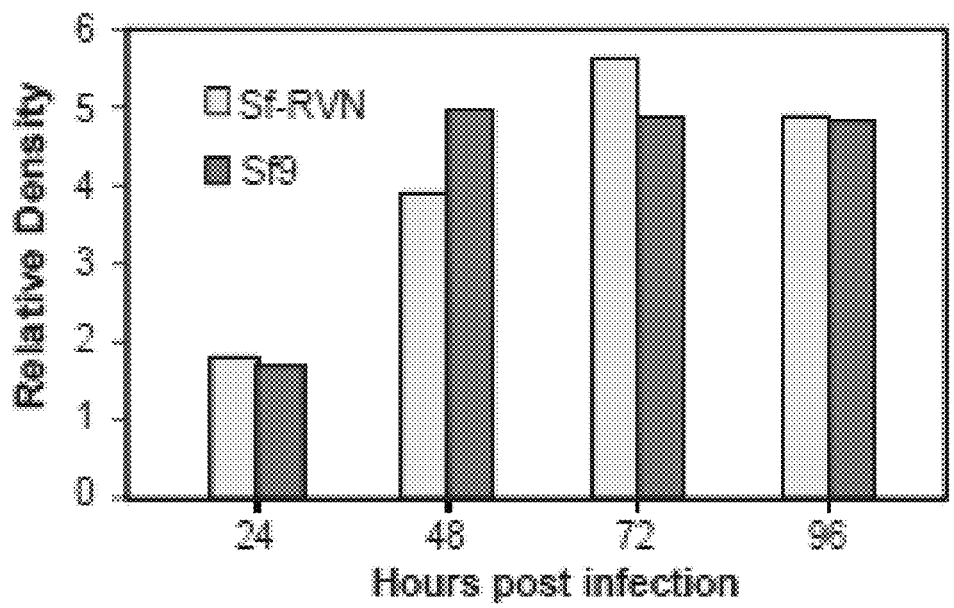

Our analysis of hSEAP production and secretion during 4 days of infection yielded essentially the same results. In this case, we expanded the experiment to include both low (0.1 pfu/cell; FIGS. 8A, 8B, and SC) and high (5 pfu/cell; FIGS. 8D, SE, and SF) MOI infections because some investigators have reported higher productivity with low, rather than conventional high MOI infections in the BIGS. The results of these experiments showed there were no statistically significant differences in the levels of hSEAP activity produced by Sf-RVN and Sf9 cells infected at either low (FIG. 8A) or high (FIG. 8D) MOIs. Representative immunoblotting results indicated Sf9 produced slightly more hSEAP when infected at low (FIGS. 8B and SC) and Sf-RVN produced slightly more hSEAP when infected at high (FIGS. 8E and 8F) MOI. However, these were only minor differences, which were not completely reproducible in an independent biological replicate of this experiment (data not shown). Both Sf-RVN and Sf9 cells produced more hSEAP activity and immunoreactive extracellular protein at 1 day and about 3-fold more hSEAP activity by 4 days post-infection when infected at high MOI. We also noted there were no differences in the viabilities of Sf-RVN and Sf9 cells during 4 days of infection at either MOI, as shown in FIGS. 6A-6B, which was derived from data obtained as part of the hSEAP expression and secretion experiments described here.

Figure 9A:
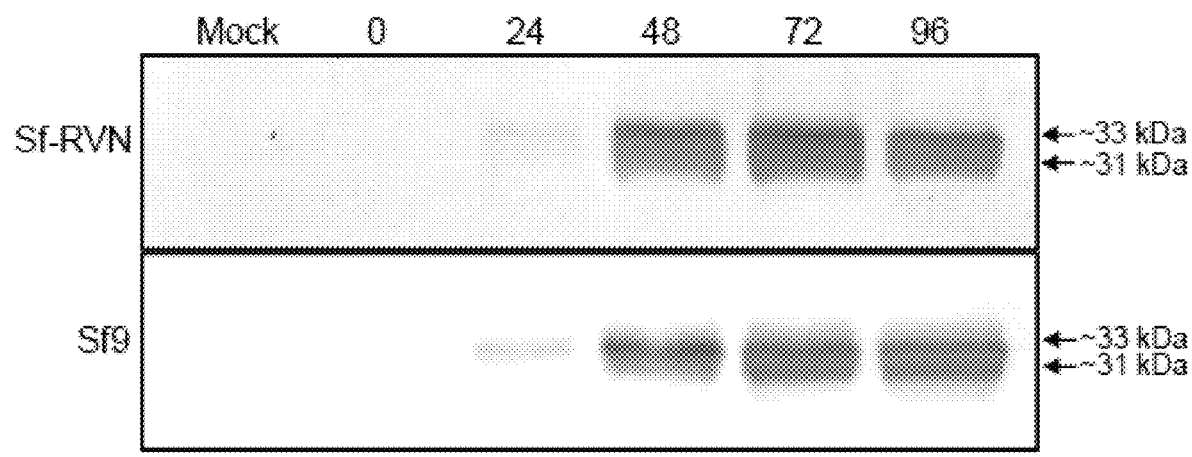
FIGS. 9A-9B: Recombinant hEPO production. Sf-RVN and Sf9 cells were infected with an St-rhabdovirus-free stock of AcP(−)p6.9hEPO at an MOI of 5 pfu/cell. Samples were harvested at various times post-infection and cell-free media were prepared and assayed for total extracellular hEPO production levels by immunoblotting analysis (FIG. 9A), with scanning laser densitometry (FIG. 9B) to estimate relative immunoreactive band densities, as described in Example 9.
Figure 9B:
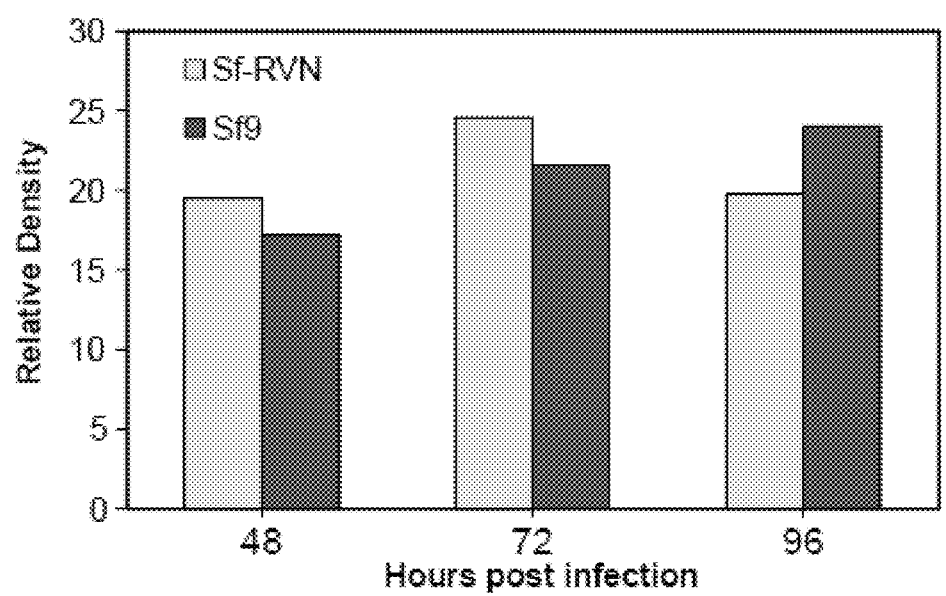

Finally, we obtained the same general results when we compared the levels of hEPO production and secretion by Sf-RVN and Sf9 cells. As there is no simple functional assay for this product, our analysis was limited to comparing the levels of immunoreactive hEPO secreted into the extracellular media by the two different cell types during a 4-day infection. The results of two independent biological replicates of this experiment revealed no major reproducible differences in the levels of secreted hEPO produced by Sf-RVN and Sf9 cells (FIGS. 9A and 9B).

Together, these results demonstrated that Sf-RVN and Sf9 cells produce and secrete three different recombinant proteins at nearly identical levels.

Example 10. N-glycan analysis. Fifty ml shake flask cultures of Sf-RVN and Sf9 cells were infected with Sf-rhabdovirus-free stocks of AcP(−)p6.9hEPO and hEPO was affinity purified from the cell- and virus-free supernatants using Ni-NTA resin (ThermoFisher). N-glycans were enzymatically released from the purified hEPO preparations by digestion with PNGase-F (New England Biolabs), and the released N-glycans were purified, derivatized, and analyzed by MALDI-TOF-MS according to known methods. Structures were assigned to peaks based on predicted masses and knowledge of the N-glycans produced in Sf cells, annotated using the standard cartoon symbolic representations, and numbered for simplicity. Relative quantification of different structures was accomplished by dividing the combined peak intensities from isotopic clusters of individual permethylated N-glycan structures by the total intensity of all annotated N-glycan peaks.

Figure 10A:
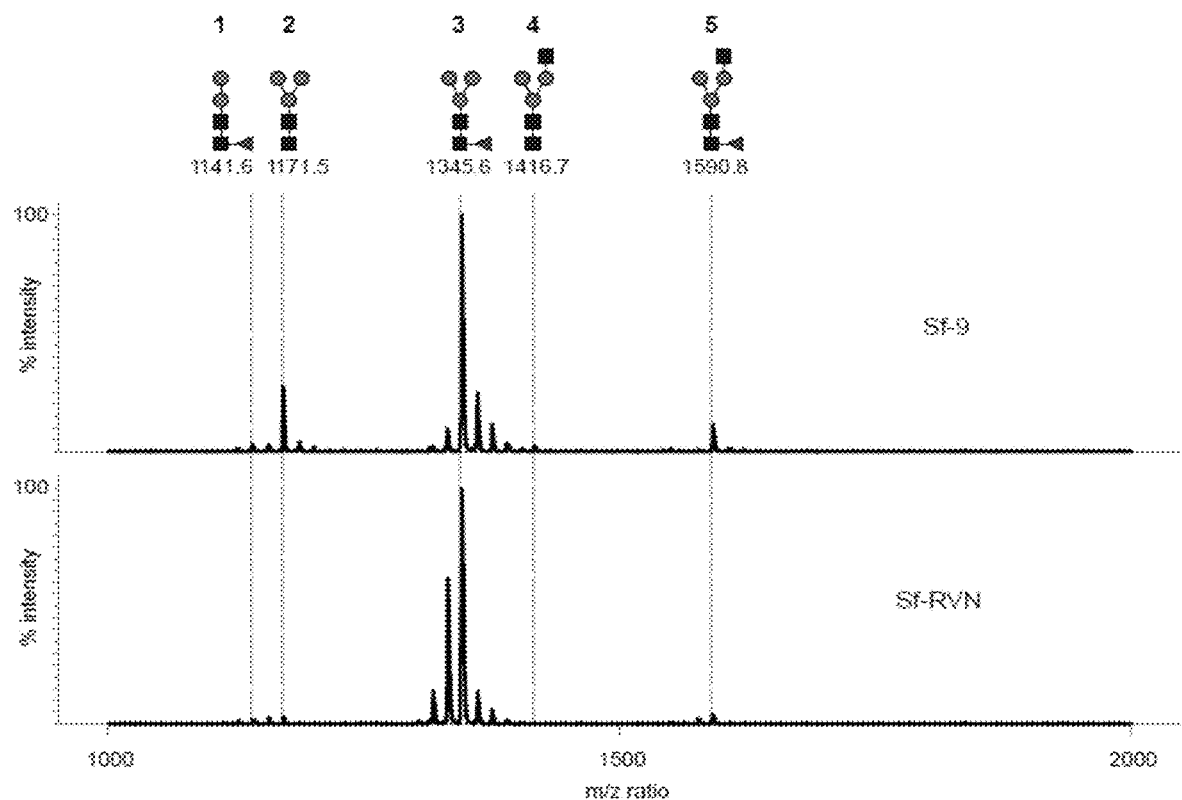
FIGS. 10A-10B: N-glycosylation profiles. Sf-RVN and Sf9 cells were infected with an Sf-rhabdovirus-free stock of AcP(−)p6.9hEPO at an MOI of 3 pfu/cell and hEPO-His was affinity-purified from the cell free media, as described in Example 10. N-glycans were enzymatically released, recovered, permethylated, and analyzed by MALDI-TOF MS (FIG. 10A), according to known methods with molecular ions detected as [M+Na]+ assigned structures, annotated using the standard cartoon symbolic representations, numbered for simplicity, and presented as percentages of total (FIG. 10B).
Figure 10B:
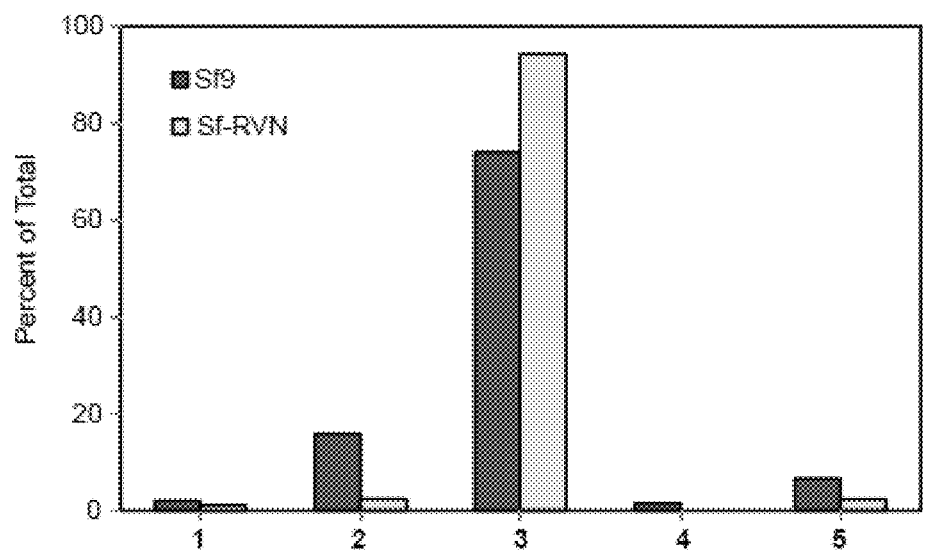

Another important factor to assess in comparing Sf-RVN and Sf9 cells is their protein N-glycosylation patterns, as the patterns provided by different cell lines can be dramatically different. Thus, we infected Sf9 and Sf-RVN cells with AcP(−)p6.9hEPO, purified the secreted hEPO from the cell-free media, enzymatically released total N-glycans, and analyzed the permethylated products by MALDI-TOF MS. The results showed the vast majority of the N-glycans linked to the hEPO produced by both cell lines had trimannosyl core structures (structures 2 and 3 in FIG. 10A), as expected. We also observed small proportions of hybrid-type structures with a terminal N-acetylglucosamine residue (structures 4 and 5 in FIG. 10A), as expected. By quantifying these different structures, we determined the hEPO N-glycosylation profiles provided by Sf-RVN and Sf9 cells were nearly identical, although the Sf-RVN cell product had slightly more fucosylated N-glycans (FIG. 10B).

Example 11. Sf-RVN cells produce more infectious baculovirus progeny. In addition to their utility as hosts for recombinant protein production, Sf9 cells are widely considered to be among the best hosts for production of baculovirus stocks. Thus, it was of interest to compare the amounts of infectious recombinant baculoviral vector progeny produced by Sf9 and Sf-RVN cells. This experiment involved infecting both cell types with two different Sf-rhabdovirus-free baculovirus stocks, AcP(−)p6.9hEPO and AcP(−)p6.9hSEAP, harvesting the budded viral progeny, i.e., cell culture media comprising infectious recombinant baculovirus, from all four infections, and comparing the infectious viral titers in plaque assays, as described in Example 8. The results of three independent biological replicates showed the working stocks of both baculoviruses, AcP(−)p6.9hEPO and AcP(−)p6.9hSEAP, had about 5-10 fold higher titers when produced by Sf-RVN, as compared to those produced by Sf9 cells (FIG.

Example 12. BLAST Searches. Bioinformatics searches of the Sf cell genome and transcriptome were conducted using the publicly accessible NCBI BLASTN interface (blast.ncbi.nlm.nih.gov/blast/Blast.cgi). The Sf-21 cell line transcribed sequence assembly (Genbank accession number GCTM00000000.1, BioProjectID 271593 (Kakumani et al., Biol. Direct 10, 1-7, 2015) and a *Spodoptera frugiperda* caterpillar head transcribed sequence assembly (Genbank accession number GESP00000000.1, BioProjectID 318819 (Cinel et al.)) were queried with the published Sf-rhabdovirus genome (Genbank accession number NC_025382.1) using megablast with the default settings.

Results obtained from a megaBLAST search using the published Sf-rhabdovirus genome (Genbank accession number NC_025382.1) as the query against the IPLB-SF-cell line transcribed sequence assembly (Genbank accession number GCTM00000000.1, BioProjectID 271593 (Kakumani et al., Biol. Direct 10, 1-7, 2015) are shown in Table 2.

TABLE 2

| Max score | Total score | Query coverage | E value | Identity | Accession |
|---|---|---|---|---|---|
| 12521 | 24213 | 97% | 0.0 | 99% | GCTM01002581.1 |

These results indicate the Sf-21 cell line transcriptome includes the intact, assembled Sf-rhabdovirus genome. Since the Sf-21 cell line was previously shown to be persistently infected with Sf-rhabdovirus, this result was expected.

Results obtained from a megaBLAST search using the published Sf-rhabdovirus genome (Genbank accession number NC_025382.1) as the query against the assembled whole brain gene expression profiles of male post-emergence *Spodoptera frugiperda* adults (fall armyworm), obtained from the National Center for Biotechnology Information BioProject PRJNA318819 (Cinel et al.) are shown in Table 3.

TABLE 3

| Max score | Total score | Query coverage | E value | % Identity | Accession No. |
|---|---|---|---|---|---|
| 17941 | 17941 | 76% | 0.0 | 98% | GESP01110283.1 |
| 17930 | 17930 | 76% | 0.0 | 98% | GESP01110282.1 |
| 10471 | 10471 | 44% | 0.0 | 98% | GESP01110281.1 |
| 5208 | 5208 | 22% | 0.0 | 98% | GESP01028237.1 |
| 965 | 965 | 4% | 0.0 | 98% | GESP01002842.1 |
| 905 | 905 | 3% | 0.0 | 98% | GESP01008203.1 |
| 734 | 734 | 3% | 0.0 | 97% | GESP01008495.1 |
| 667 | 667 | 2% | 0.0 | 99% | GESP01141621.1 |
| 608 | 608 | 2% | 1e−171 | 98% | GESP01110280.1 |
| 586 | 586 | 2% | 5e−165 | 98% | GESP01135659.1 |
| 551 | 551 | 2% | 2e−154 | 98% | GESP01137160.1 |
| 549 | 549 | 2% | 7e−154 | 98% | GESP01139133.1 |
| 521 | 521 | 2% | 2e−145 | 94% | GESP01110279.1 |

To our surprise, several assembled sequences were detected in the transcriptome of these organisms, which collectively comprise an intact Sf-rhabdovirus genome. These data show the caterpillar (*Spodoptera frugiperda*), from which all Sf cell lines are derived, is itself infected with Sf-rhabdovirus. Thus, the reason all cell lines derived from *Spodoptera frugiperda* are contaminated with Sf-rhabdovirus is the organism was naturally infected with this virus in the environment before the first Sf cell line was isolated, not because the cell line(s) were contaminated with the virus in the laboratory.

In stark contrast, a BLAST search of the Sf-RVN transcriptome with Sf-rhabdovirus sequence as a query produced no hits, further substantiating our finding that Sf-RVN cells are not contaminated with Sf-rhabdovirus. The BLAST search results are summarized in Table 4. Since all Sf cell lines previously tested previously tested by our lab and others were shown to be positive for Sf-rhabdovirus contamination, the absence of Sf-rhabdovirus sequences in the transcriptome of the Sf-RVN cell line clearly demonstrates these cells are structurally (genetically) different from any other Sf cell line and from *Spodoptera frugiperda*, the naturally-occurring organism from which all previously described Sf cell lines are derived. This structural difference is substantiated by the fact that the Sf-RVN cells are susceptible to Sf-rhabdovirus infection.

TABLE 4

BLAST Search Results for Sf-rhabdovirus

| Test Sample | Reads mapped to Sf-rhabdovirus | Total number of reads | % Sf-rhabdovirus |
| --- | --- | --- | --- |
| Sf brainsa | $380 \times 10^3$ | $480 \times 10^6$ | 0.63 |
| Sf-21 cellsb | $259 \times 10^3$ | $230 \times 10^6$ | 0.11 |
| Sf-RVN cells | 0 | $453 \times 10^6$ | 0 | aNCBI BioProjectID 318819;
bKakumani et al.

Example 13. The Sf-RVN cell line is susceptible to infection by Sf-rhabdovirus. Sf9 cells were seeded at a starting density of $1.0 \times 10^6$ cells per ml in TNM-FH medium supplemented with 10% (v/v) fetal bovine serum (Atlanta Biologicals, Inc., Flowery Branch, Ga.) in a 50 ml shake-flask culture. The cells were incubated at 28° C. in a shaker incubator for 3 days. After incubation, the cells were pelleted by low speed centrifugation and the cell-free supernatants were filtered through a 0.22 μM filter (CELLTREAT Scientific, Shirley, Mass.). This filtrate was used as Sf-rhabdovirus inoculum to examine the susceptibility of Sf-RVN cells to this virus.

For the infectivity experiment, Sf-RVN cells were seeded in duplicate at a density of $2.0 \times 10^6$ cells in 5 ml of ESF921 medium (Expression Systems, Woodland, Calif.) in 25 cm² flasks and incubated for 1 h at 28° C. to allow the cells to adhere. The growth medium was then removed and the cells in replicate flasks were either: (1) mock-infected with 2.5 ml of TNM-FH medium supplemented with 10% (v/v) fetal bovine serum or (2) infected with 2.5 ml of the Sf-rhabdovirus inoculum described above. The cells were incubated for 2 h at 28° C. and then 2.5 ml of fresh TNM-FH medium supplemented with 10% (v/v) fetal bovine serum were added and the cells were incubated for another 24 h at 28° C. At 24 h post-infection, one set of mock- or Sf-rhabdovirus inoculum-infected cells was washed three times and harvested. The second set was further incubated at 28° C., sampled and serially passaged (PO to P1) at 72 h post-infection, and then sampled and serially passaged again after two additional 72 h incubation periods until a total of three passages were done. The samples obtained at each passage level were used to produce cell pellets by low speed centrifugation, total RNA was extracted, and samples were assayed by RT-PCR, as described in Example 4.

Figure 13A:
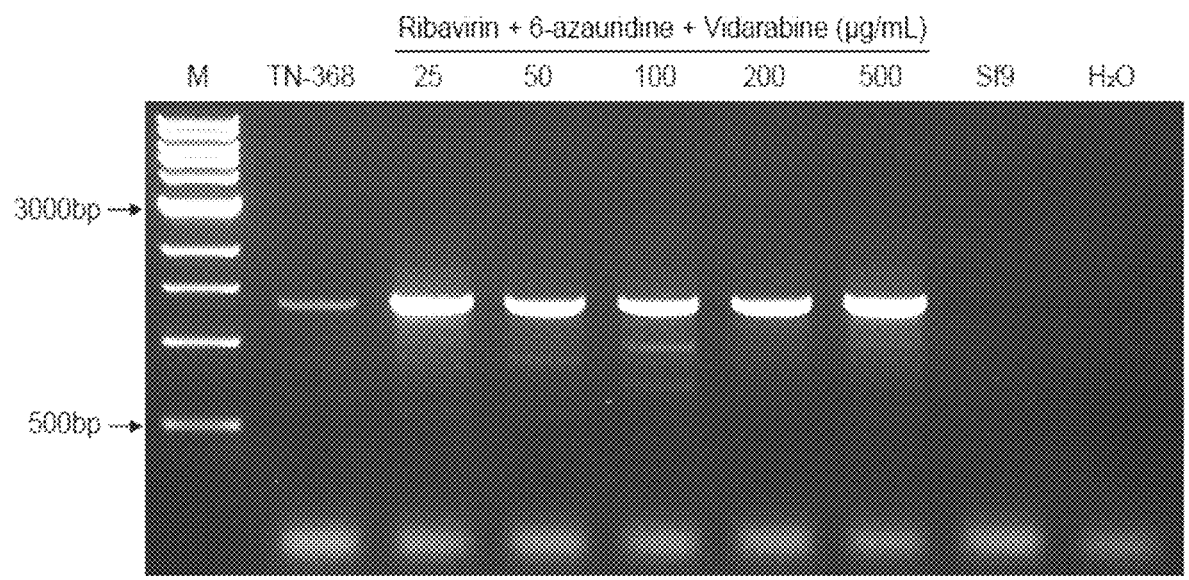
FIGS. 13A-13B: Tn-nodavirus in polyclonal TN-368 cells treated with antiviral drugs. Polyclonal TN-368 cell populations were treated for 15 days with various concentrations of a cocktail of three antiviral drugs, ribavirin, 6-azauridine, and vidarabine. Total RNA was extracted from cells that were still being cultivated in the presence of these drugs and assayed for Tn-nodavirus RNA segment 1 (FIG. 13A) or 2 (FIG. 13B) by RT-PCR, as described in Example 16. Total RNAs extracted from TN-368 or Sf9 cells were used as positive or negative controls, respectively. An additional negative control reaction was performed with no template (H2O). Lanes marked "M" show the 100-bp markers, with selected sizes indicated on the left.
Figure 13B:
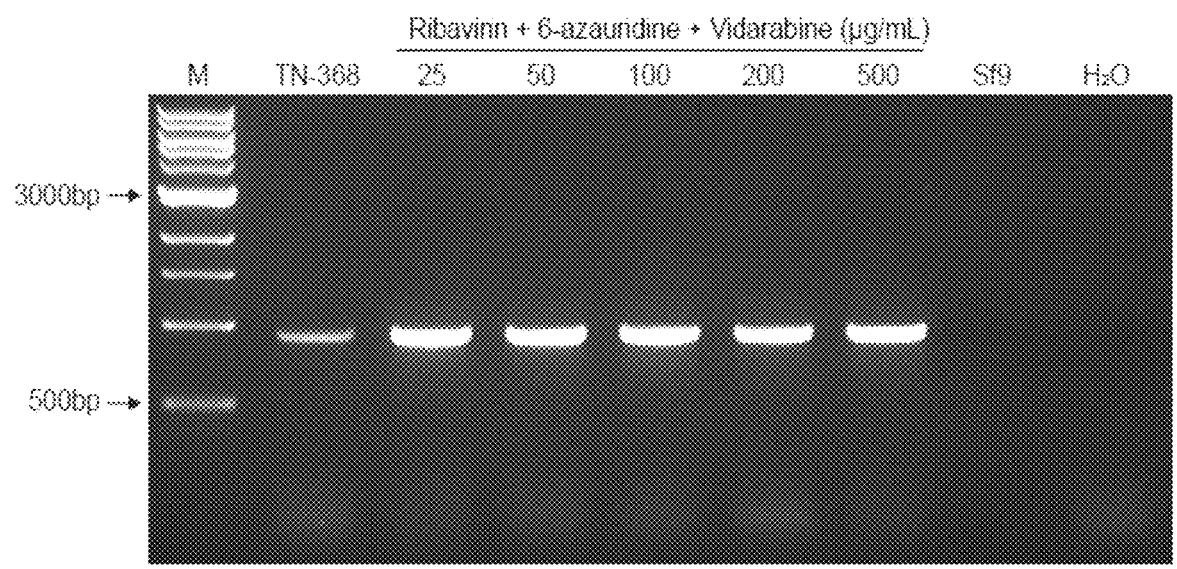

No Sf-rhabdovirus specific amplicon was observed with RNA obtained from mock-infected Sf-RVN cells at any time point or with RNA obtained from the Sf-rhabdovirus inoculum-infected PO Sf-RVN cells at either 24 or 72 h post-infection (FIGS. 13A-13B). However, a faint amplicon was observed with RNA obtained from the Sf-rhabdovirus inoculum-infected Sf-RVN cells at 72 h after P1 and it intensity progressively increased with RNA obtained at 72 h after P2 and at 72 h after P3 (FIGS. 13A-13B). These results clearly demonstrate Sf-RVN cells are susceptible to infection with Sf-rhabdovirus produced by contaminated Sf cells.

Example 14. Conventional methods fail to produce a virus-free established *T. ni* cell line. We also attempted to isolate Tn-nodavirus-free cells by culturing polyclonal TN-368 cell populations in TNM-FH medium supplemented with 10% (v/v) fetal bovine serum plus various concentrations of a cocktail of antiviral drugs including ribavirin, 6-azauridine, and vidarabine. The cells were cultured with these three drugs for 15 days with ad hoc serial passages and samples were routinely tested for Tn-nodavirus by RT-PCR, as described in Example 16. As shown in FIGS. 13A-13B, amplicons corresponding to Tn-nodavirus segments 1 and 2 were present in TN-368 cells that had been incubated in all concentrations of the antiviral cocktail tested (FIGS. 13A and 13B, respectively). Thus, as with Sf9 cells, we could not obtain nodavirus-free *T. ni* cells using populations of TN-368 cells treated with this antiviral cocktail.

Figure 14A:
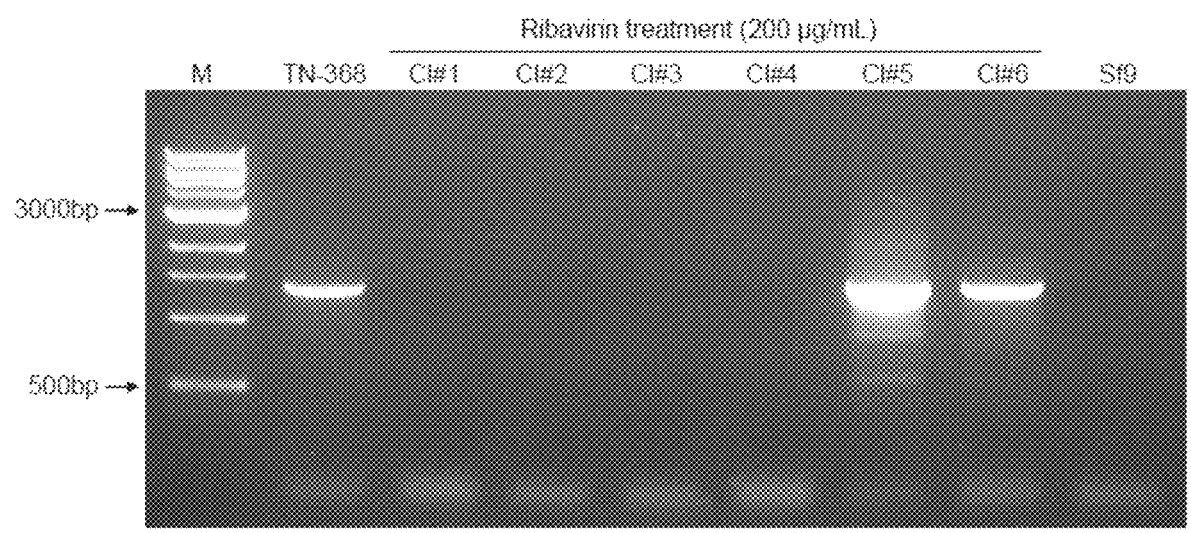
FIGS. 14A-14B: Absence of Tn-nodavirus in ribavirin-treated TN-368 subclones. Total RNA was isolated from six single cell TN-368 subclones treated for one month with 200 µg/ml of ribavirin. Samples were then assayed for Tn-nodavirus RNA segment 1 by RT-PCR (FIG. 14A) or RT-PCR, followed by nested PCR (FIG. 14B), as described in Example 16. Total RNAs extracted from TN-368 or Sf9 cells were used as positive or negative controls, respectively. Lanes marked "M" show the 100-bp markers, with selected sizes indicated on the left.
Figure 14B:
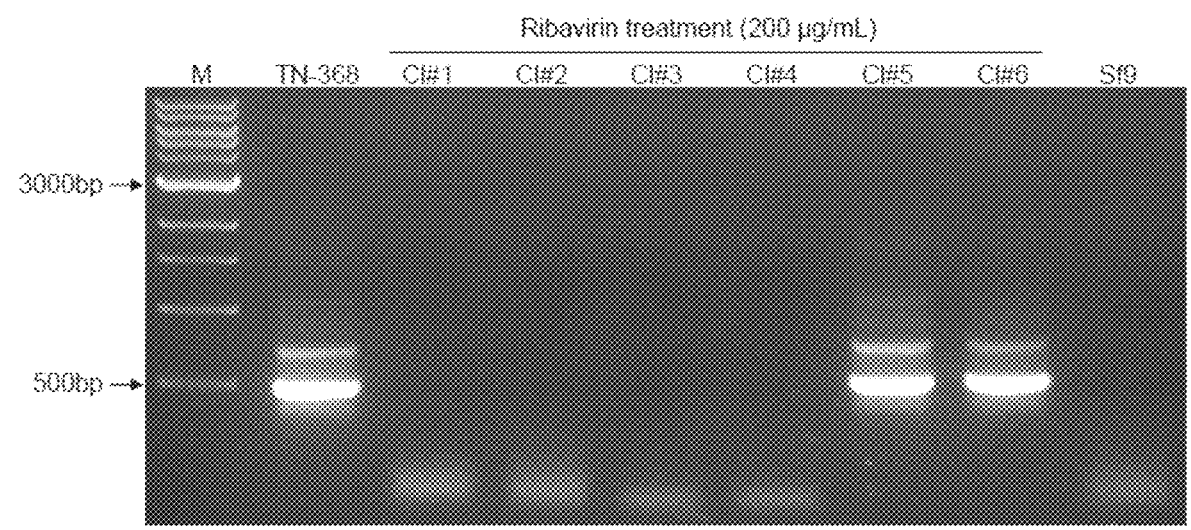

Example 15. Exemplary method for obtaining an established *T. ni* cell line that lacks virus. After discovering polyclonal TN-368 cell cultures treated with antiviral drug cocktails remained Tn-nodavirus-positive, we employed a disclosed method for obtaining a virus-free cell line. This exemplary method embodiment comprised isolating single TN-368 cells by limiting dilution to isolate single cells, seeding the isolated cells into 96-well plates in TNM-FH medium supplemented with 10% (v/v) fetal bovine serum and 200 μg/mL of ribavirin to form a first culture composition. The first culture composition was cultured for about a month with ad hoc amplification to produce progressively larger cultures and, after achieving the 25 cm² flask level, samples were tested for Tn-nodavirus by RT-PCR, followed by nested PCR, as described in Example 16. A clone lacking Tn-nodavirus (FIG. 14A, lane CL #3) was transferred to media lacking antiviral drugs to form a second culture composition. The clone, designated Tn-NVN passage zero (PO), was adapted to serum-free ESF 921 medium and grown in suspension. The Tn-NVN cell line was subsequently maintained in this second culture composition and growth format.

Example 16. Tn-nodavirus-specific Reverse Transcription-PCR (RT-PCR)/nested PCR. Samples of TN-368 and Tn-NVN cultures containing $1 \times 10^6$ cells were harvested and the cells were pelleted by low speed centrifugation. The cell-free supernatants were filtered through a 0.22 μm filter (CELLTREAT Scientific, Shirley, Mass.) and then ultracentrifuged at 131,000×g for 22 h at 4° C. Total RNA was extracted from both the low speed cell and high speed cell-free pellets using the RNASo/v reagent (Omega Bio-Tek, Inc., Norcross, Ga.), according to the manufacturer's protocol. The RNAs were then quantified and used as templates for cDNA synthesis with the ProtoScript II First Strand cDNA synthesis kit (New England Biolabs, Ipswich, Mass.) and a Tn-nodavirus-specific primer designated Noda-7 (SEQ ID NO: 24), according to the manufacturer's protocol. Equivalent amounts of each cDNA preparation were used for nested PCR's with Taq DNA polymerase, ThermoPol reaction buffer (New England Biolabs), and Tn-nodavirus RNA segment 1—(Noda-1; SEQ ID NO: 19 and Noda-2; SEQ ID NO: 20) or segment 2—(Noda-6; SEQ ID NO: 23 and Noda-7; SEQ ID NO: 24) specific primer pairs. The reaction mixtures were incubated at 94° C. for 3 min, cycled 35 times at 94° C. for 30 s, 60° C. for 1 min, and 72° C. for 1 min, and finally incubated at 72° C. for 10 min. One μL of each primary PCR was then used as the template for nested PCR's under the same conditions with Tn-nodavirus RNA segment 1—(Noda-1i; SEQ ID NO: 21 and Noda-2i; SEQ ID NO: 22) or segment 2—(Noda-6i; SEQ ID NO: 25 and Noda-7i; SEQ ID NO: 26) specific primer pairs. The RT-PCR and RT-PCR followed by nested PCR products were analyzed by agarose gel electrophoresis with ethidium bromide staining according to standard methodology. The sequence of each primer used for these assays is shown in Table 5.

TABLE 5

Tn-nodavirus-specific primers

| Primer | Sequence (5' to 3') | Product Size (bp)[1] |
|---|---|---|
| Noda-1 | GGG AAC CGA GIT ACA CGC GCATTG C (SEQ ID NO: 19) | 1342 bp |
| Noda-2 | CCG CCC TAA GIT GIA GIT GIT GGG ACG G (SEQ ID NO: 20) | |
| Noda-1i | GAT GCT GAC TCA CCAITC ACC (SEQ ID NO: 21) | 503 bp |
| Noda-2i | CCG ATA AGC CIA GCG TTG ACAGAT TG (SEQ ID NO: 22) | |
| Noda-6 | GCC ITC GCA CCA CCI GAC ITC (SEQ ID NO: 23) | 951 bp |
| Noda-7 | GCC AGG AAT GIT GCT TGCAAC AGC (SEQ ID NO: 24) | |
| Noda-6i | CAT CCA GAT CCG ATC AAGTGT C (SEQ ID NO: 25) | 432 bp |
| Noda-7i | CAC GGA TGA CAA TGG TGT CC (SEQ ID NO: 26) | |

[1]Size of the amplification products resulting from PCR with odd/even primer pairs.

Figure 15A:
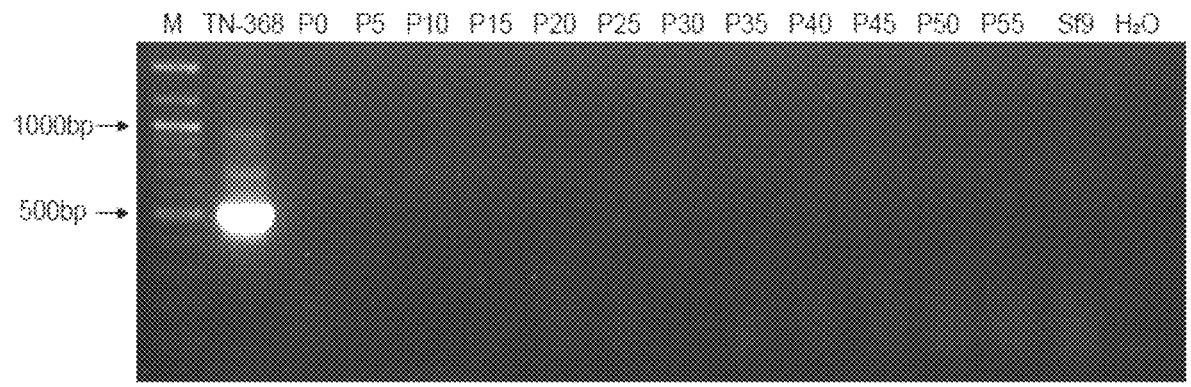
FIGS. 15A-15C: Absence of Tn-nodavirus in Tn-NVN cells. Total RNA was isolated from an exemplary cell line, referred to as "Tn-NVN", cultured for various passages in the absence of antiviral drugs and assayed for the presence of Tn-nodavirus by RT-PCR, followed by nested PCR with primers specific for Tn-nodavirus segment 1 (FIG. 15A) or segment 2 (FIG. 15B), as described in Example 16. This exemplary cell line, referred to as Tn-NVN, was generated by expanding a ribavirin-treated TN-368 clone (CI #3), which was found to be negative for Tn-nodavirus contamination (FIGS. 15A-15C). The Tn-nodavirus-specific RT-PCR, followed by nested PCR, results demonstrated no Tn-nodavirus was present after 55 passages of the Tn-NVN cells (FIGS. 15A and 15B). We also isolated total RNA from the pellet fraction obtained by ultracentrifuging the CFM from Tn-NVN cells at passage 55 and used it to assay for Tn-nodavirus using the Tn-nodavirus-specific RT-PCR, followed by nested PCR, as described in Example 16.
Figure 15B:
Figure 15C:
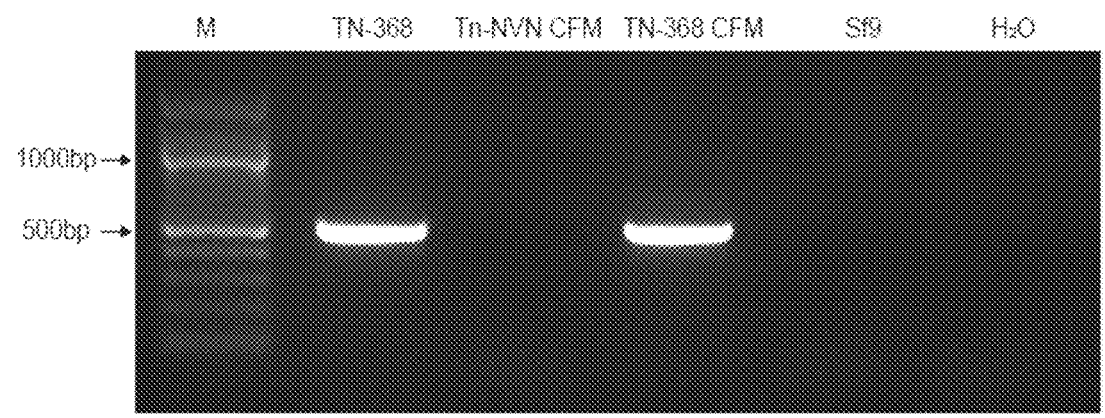

Example 17. Tn-NVN cells have no detectable Tn-nodavirus. Total RNA was isolated from Tn-NVN at various passage levels and assayed for the presence of Tn-nodavirus by RT-PCR, followed by nested PCR with primers specific for Tn-nodavirus segment 1 (FIG. 15A) or 2 (FIG. 15B), as described in Example 16. The Tn-nodavirus-specific RT-PCR/nested PCR results demonstrated Tn-NVN cells had no detectable Tn-nodavirus for at least 55 serial passages in the absence of any antiviral drugs (FIGS. 15A-15C). We also isolated total RNA from the pellet fraction obtained by ultracentrifuging the cell-free media (CFM) from Tn-NVN cells at passage 55 and used it to assay for Tn-nodavirus using the Tn-nodavirus-specific RT-PCR/nested PCR, as described in Example 16. As shown in FIG. 15C, a Tn-nodavirus amplicon was observed in the lanes corresponding to RNA isolated from TN-368 cells and from the TN-368 cell-free media pellet. In contrast, the Tn-nodavirus amplicon was not detected in the RNA isolated from the Tn-NVN cell-free media pellet. All results shown in FIGS. 15A-15C were obtained using RNA from cells cultivated in the absence of antiviral drugs. Together, these results demonstrated there was no detectable Tn-nodavirus RNA in Tn-NVN cells or cell-free media over the course of 55 passages in the absence of any antiviral drugs, which indicates these cells are Tn-nodavirus-free.

Figure 16:
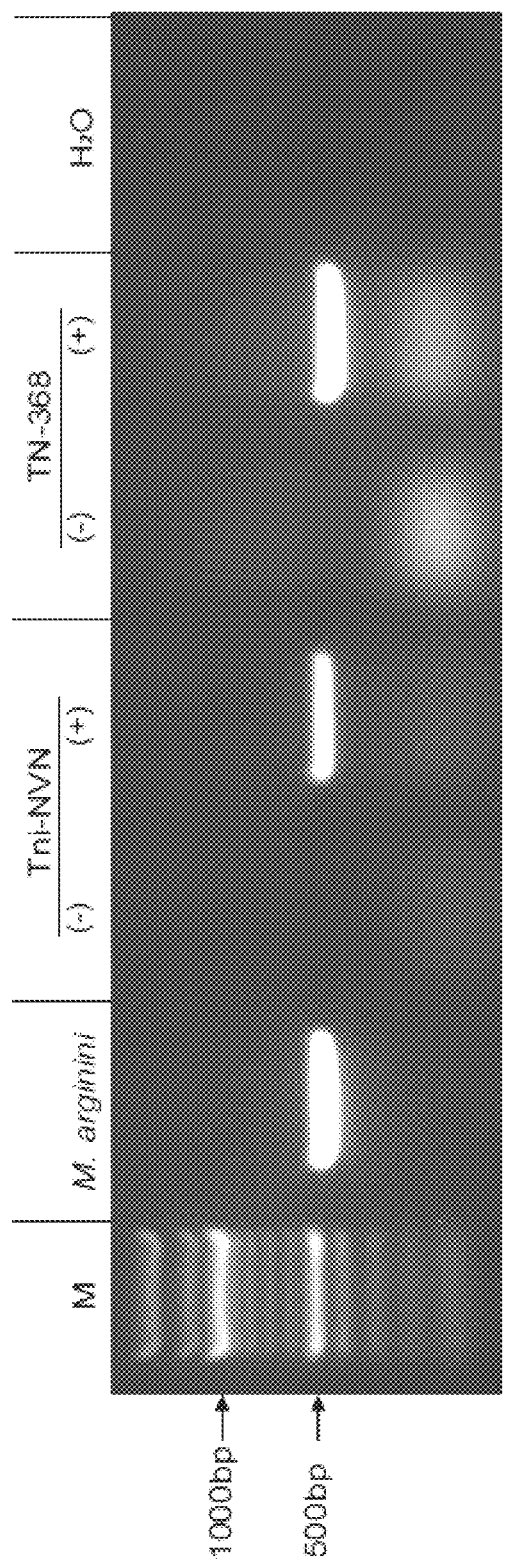
FIG. 16: *Mycoplasma* assays. Tn-NVN and TN-368 cell extracts(–) were assayed for *mycoplasma* contamination using the PCR-based Universal *Mycoplasma* Detection Kit (American Type Culture Collection), as described in Examples 6 and 18. A plasmid encoding an *M. arginini* rRNA target sequence was used as the positive control (FIG. 16, lane "*M. arginini*"). Additional controls were performed using Tn-NVN and TN-368 cell lysates spiked with this plasmid (FIG. 16, lanes Tn-NVN (+) and TN-368 (+), respectively) to determine if the lysate interfered with the assay. A negative control reaction was performed with no template (H2O). The lane marked M shows the 100-bp markers, with selected sizes indicated on the left.

Example 18. *Mycoplasma* detection. We also tested samples containing about $10^5$ Tn-NVN, or TN-368 cells for *Mycoplasma* using the Universal *Mycoplasma* Detection kit from ATCC (Manassas, Va.), according to the manufacturer's protocol. This PCR-based assay uses primers complementary to sequences conserved in the 16S rRNA genes of over 60 different *Mycoplasma, Acholeplasma, Spiroplasma* and *Ureaplasma* species, including eight species that are frequently found as contaminants of cell cultures. The results shown in FIG. 16 demonstrated neither the TN-368 nor the Tn-NVN cells were detectably contaminated with *Mycoplasma*. In both cases, the absence of a PCR product was not due to inhibition of the PCR reaction by the insect cell lysates, as amplicons of the expected sizes were observed in PCRs performed using lysates spiked with the control templates (FIG. 16, lanes Tn-NVN (+) and TN-368 (+)).

Figure 17A:
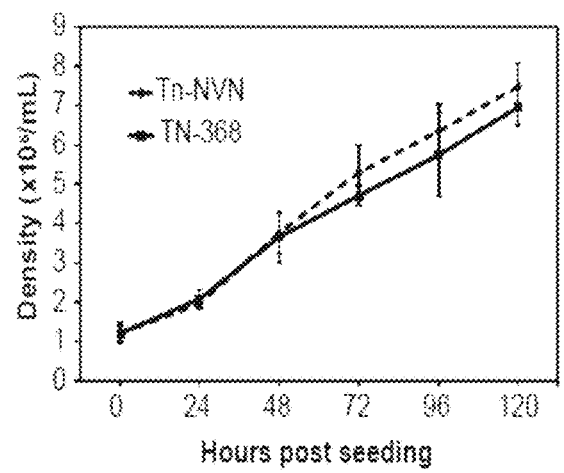
FIGS. 17A-17C: Cell growth and morphology. Tn-NVN and TN-368 cells were seeded into shake flasks at a density of $1.0 \times 10^6$ cells/ml in ESF 921 medium. Triplicate samples were harvested at various times after seeding and viable cell counts and diameters were measured with an automated cell counter, as described in Examples 7 and 19. The figure depicts the average viable cell densities (FIG. 17A) and diameters (FIG. 17B) measured in three independent experiments, as well as phase contrast micrographs of Tn-NVN and TN-368 cells at a magnification of 10X (FIG. 17C). The error bars represent the confidence intervals ($P<0.05$).
Figure 17B:
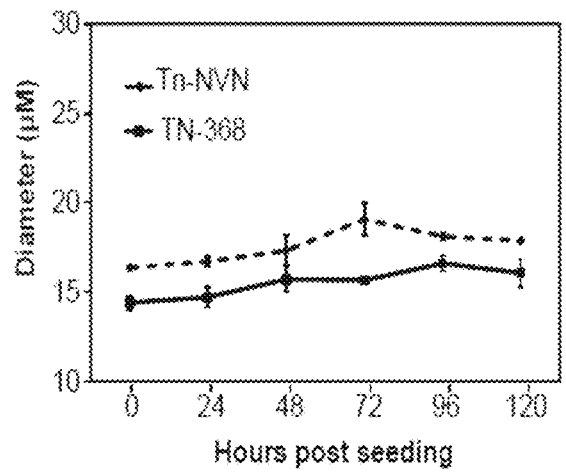
Figure 17C:
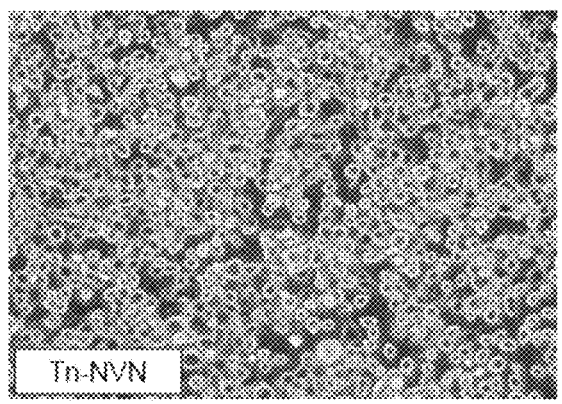
Figure 17C:
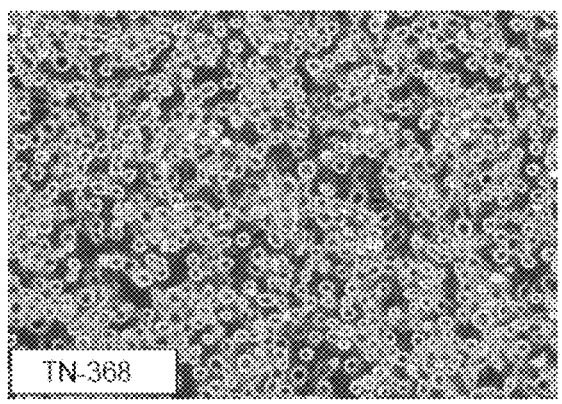

Example 19. Cell growth properties, morphologies, and diameters of Tn-NVN and TN-368 cells. We compared the general properties of Tn-NVN cells to those of TN-368, including their culture densities, diameters, and morphologies using the techniques described in Example 7. The results showed Tn-NVN and TN-368 cells achieved virtually identical average densities over the course of five days after being seeded into parallel shake flask cultures in ESF-921 medium (FIG. 17A). The results also revealed no significant differences in the average diameters (FIG. 17B) or morphologies (FIG. 17C) of Tn-NVN and TN-368 cells during the course of these cell culture experiments. Overall, these results demonstrated that the general properties of Tn-NVN and TN-368 cells examined in this study are the same or substantially the same.

Example 20. Tn-NVN and TN-368 cells produce recombinant proteins at nearly identical levels. We also compared the levels of baculovirus-mediated recombinant protein production supported by Tn-NVN and TN-368 cells, using B-gal, hSEAP, and hEPO, as described in Example 9. It is important to emphasize that Tn nodavirus-free working stocks of each of the recombinant baculoviruses were prepared and used for these studies, as described in Example 8.

Figure 18A:
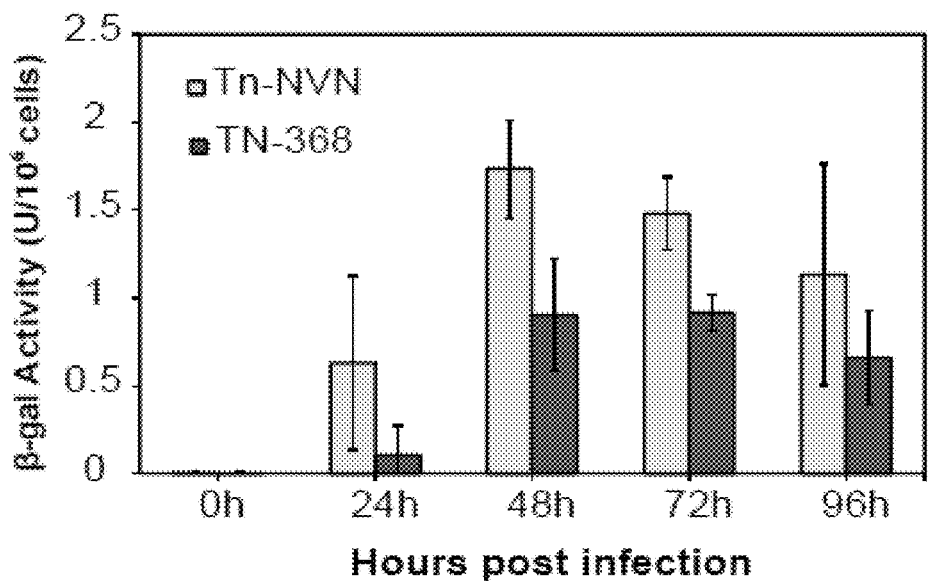
FIGS. 18A-18C: Recombinant B-gal production. Tn-NVN and TN-368 cells were infected with a Tn-nodavirus-free stock of BacPAK6-L1Chi/Cath at an MOI of 5 pfu/cell. Triplicate samples were harvested at various times post-infection and clarified intracellular extracts were assayed for 13-gal activity (FIG. 18A), as described in Examples 9 and 20. This plot shows the average results with error bars representing the confidence intervals ($P<0.05$). One set of extracts was also used to measure total intracellular B-gal production levels by immunoblotting analysis (FIG. 18B), with scanning laser densitometry (FIG. 18C) to estimate relative immunoreactive band densities. The same general trends were observed in two independent biological replicates of this experiment.
Figure 18B:
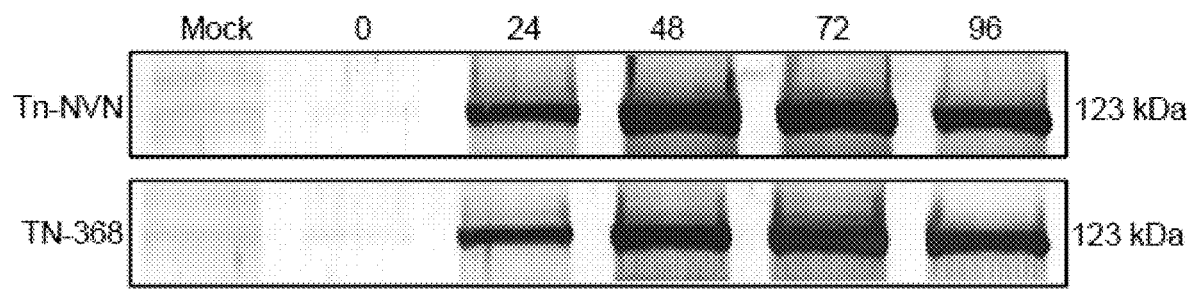
Figure 18C:
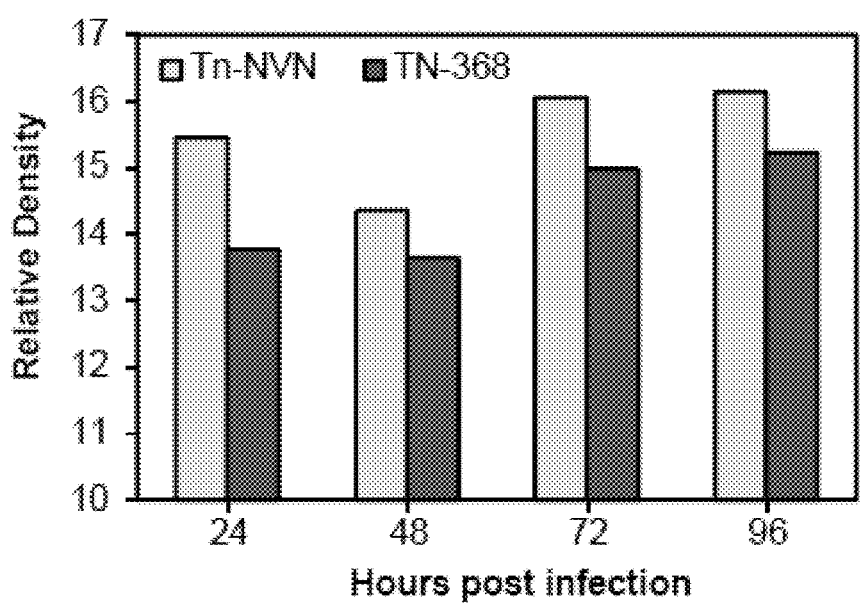

The *E. coli* B-gal expression experiments revealed no significant differences in the intracellular enzyme activity levels (FIG. 18A) or total intracellular B-gal protein (FIGS. 18B and 18C) produced by Tn-NVN and TN-368 cells over the 4 day time course of infection. Again, we noted the levels of enzyme activity and immunoreactive intracellular B-gal both decreased at 3-4 days post-infection, as compared to earlier time points, perhaps reflecting baculovirus-induced cytotoxicity at these later times of infection.

Figure 19A:
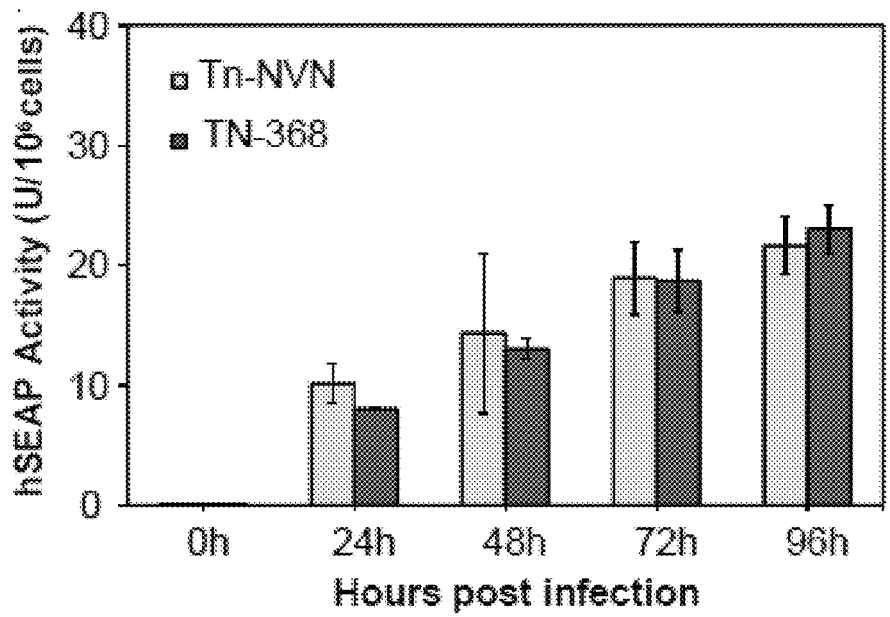
FIGS. 19A-19C: Recombinant hSEAP production. Tn-NVN and TN-368 cells were infected with a Tn-nodavirus-free stock of AcP(–)p6.9hSEAP at an MOI of 5 pfu/cell. Triplicate samples were harvested at various times post-infection, cell-free media were prepared and assayed for hSEAP activity, as described in Examples 9 and 20, and the average results were plotted with error bars representing the confidence intervals ($P<0.05$.
Figure 19B:
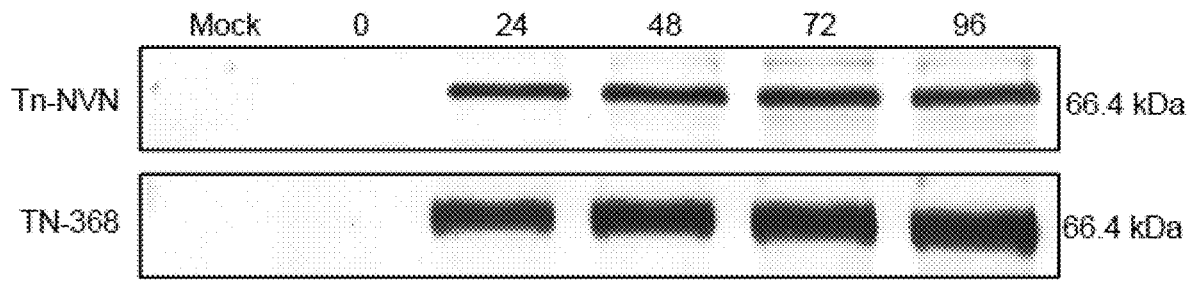
Figure 19C:
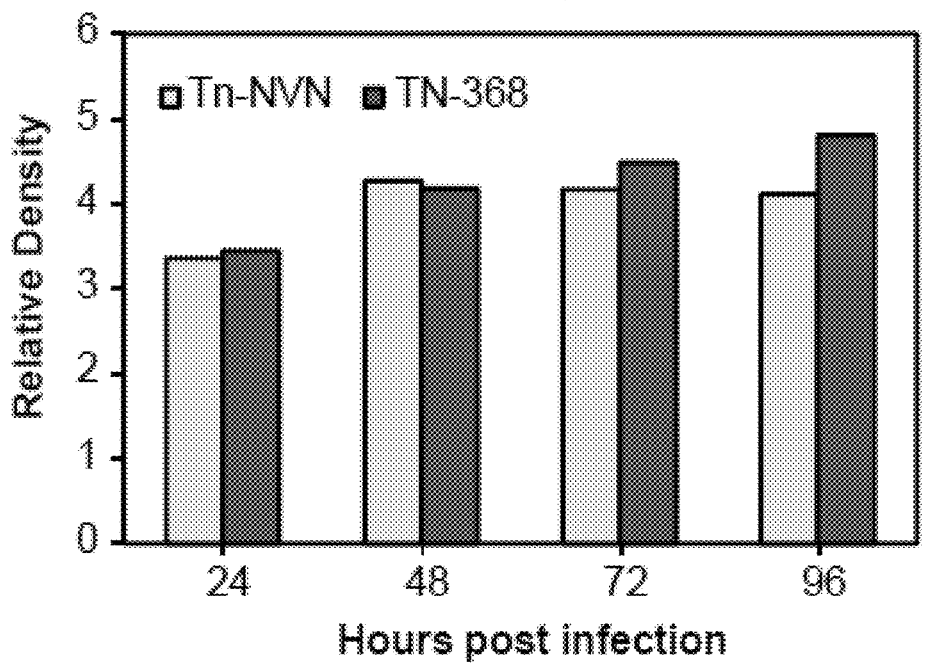

Our analysis of hSEAP production and secretion over the 4 day time course of infection yielded essentially the same results, revealing no statistically significant differences in the levels of hSEAP activity or immunoreactive secreted hSEAP protein produced by Tn-NVN and TN-368 cells (FIGS. 19A-19C).

Figure 20A:
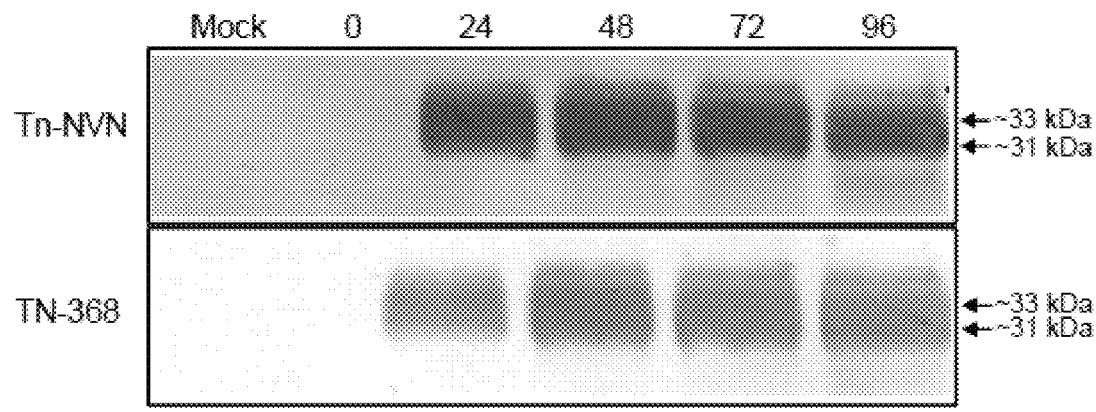
FIGS. 20A-20B: Recombinant hEPO production. Tn-NVN and TN-368 cells were infected with a Tn-nodavirus-free stock of AcP(–)p6.9hEPO at an MOI of 5 pfu/cell. Samples were harvested at various times post-infection and cell-free media were prepared and assayed for total extracellular hEPO production levels by immunoblotting analysis (FIG. 20A), with scanning laser densitometry (FIG. 20B) used to estimate relative immunoreactive band densities, as described in Examples 9 and 20.
Figure 20B:
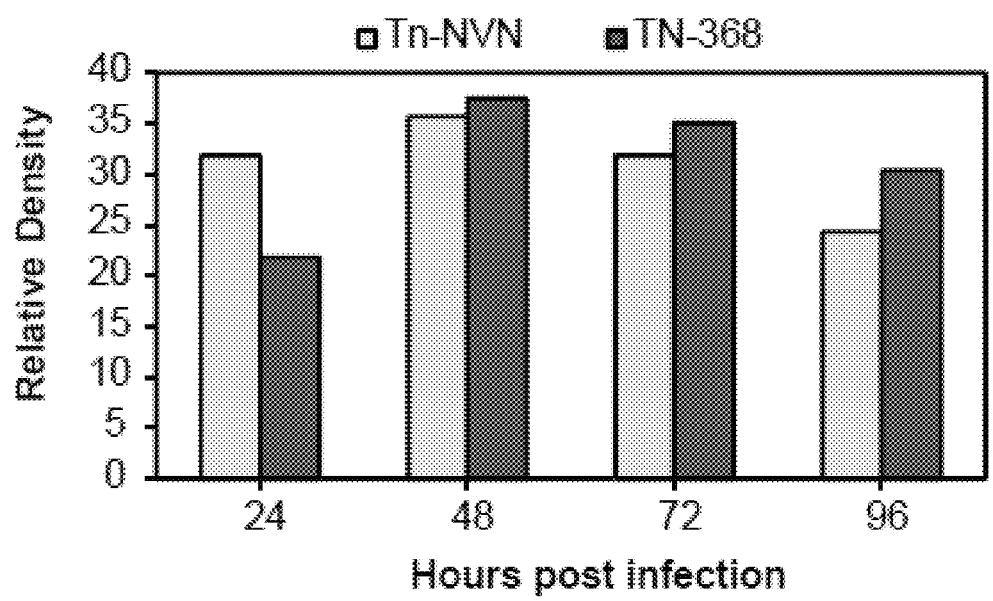

Finally, we obtained the same general results when we compared the levels of hEPO production and secretion by Tn-NVN and TN-368 cells during a 4-day infection (FIGS. 20A-20B). These results demonstrated Tn-NVN and TN-368 cells produce and secrete three different recombinant proteins at the same or substantially the same levels.

Figure 21A:
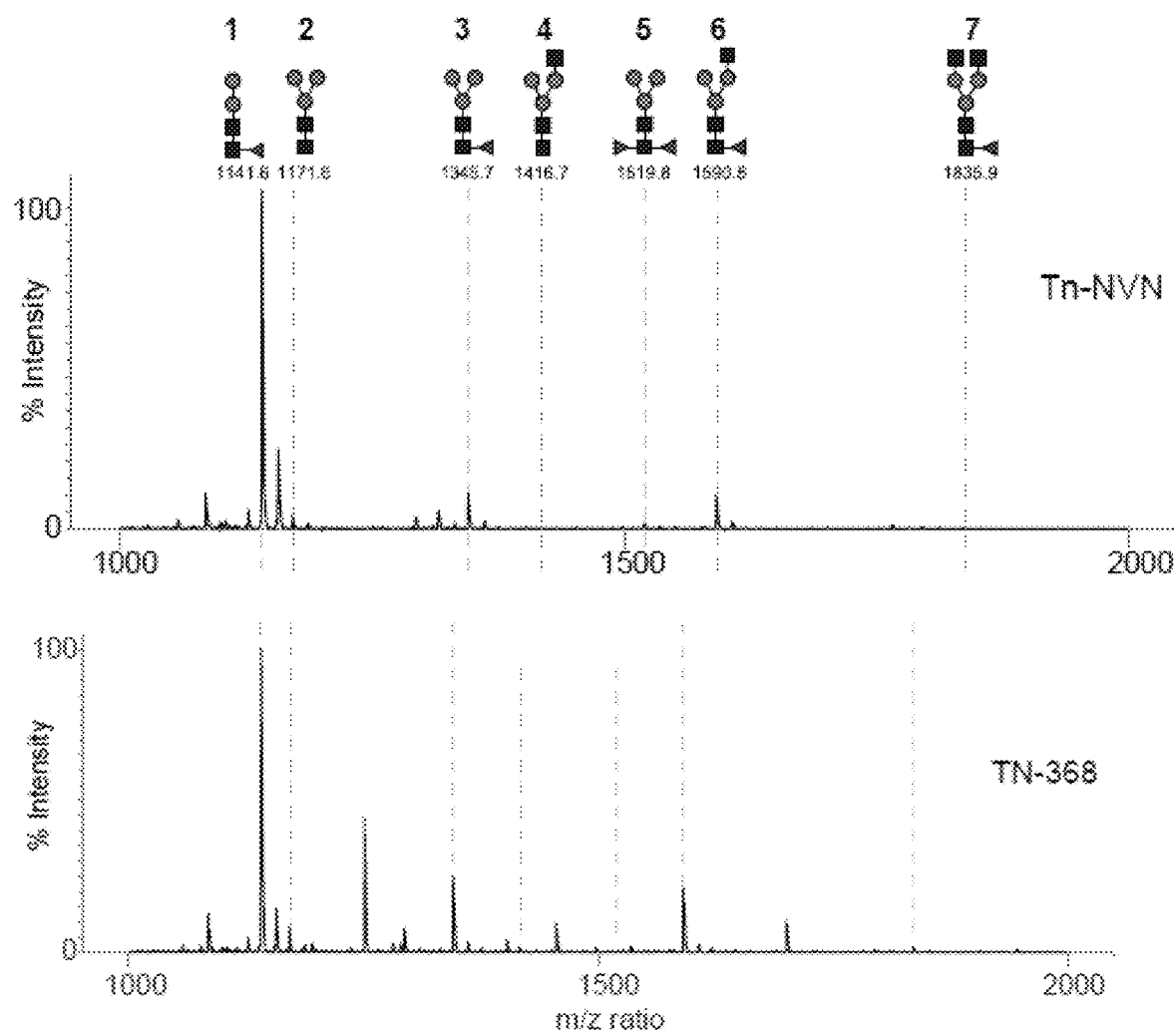
FIGS. 21A-21B: N-glycosylation profiles. Tn-NVN and TN-368 cells were infected with a Tn-nodavirus-free stock of AcP(–)p6.9hEPO at an MOI of 3 pfu/cell and hEPO-His was affinity-purified from the cell free media, as described in Examples 10 and 21. N-glycans were enzymatically released, recovered, permethylated, and analyzed by MALDI-TOF MS (FIG. 21A), according to known methods, and molecular ions detected as [M+Na]+ were assigned structures, annotated using the standard cartoon symbolic representations, numbered for simplicity, and presented as percentages of total (FIG. 21B).
Figure 21B:
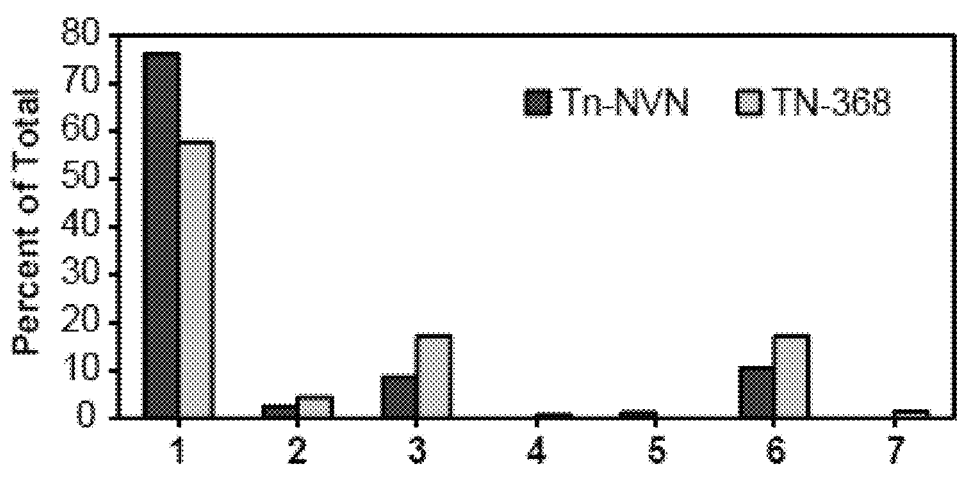

Example 21. N-glycan analysis of Tn-NVN and TN-368 cells. We analyzed the N-glycosylation profiles of Tn-NVN and TN-368 cells, as described in Example 10. MALDI- TOF-MS analysis of the N-glycans isolated from hEPO produced by Tn-NVN and TN-368 cells showed they provided essentially identical glycosylation patterns. The vast majority of the N-glycans on hEPO from both cell lines were bimannosyl core structures FIG. 21A, structure 1), but we also observed small proportions of fucosylated trimannosyl core structures with and without terminal N-acetylglucosamine residues (FIG. 21A, structures 3 and 6).

Example 22. The BmN cell line, derived from *Bombyx mori*, is infected with Sf-rhabdovirus. To investigate whether cells from the lepidopteran insect *Bombyx mori* are contaminated, we analyzed the BmN cell line for the presence of Sf-rhabdovirus. A vial of BmN cells (ATCC-CRL 8910) from our laboratory cell bank was thawed, the cells were pelleted by low speed centrifugation, and total RNAs were extracted, quantified and assayed by RT-PCR, as described in Example 4. The RT-PCRs were performed essentially as described, except in this case, independent RT-PCRs were performed with primers specific for all six of the Sf-rhabdovirus genes (Table 6).

TABLE 6

Sf-rhabdovirus-specific primers

| Sf-Rhabdo Gene | Primer | Sequence (5' to 3') |
|---|---|---|
| N | NSP | GAG TGT TGA TAC ATG TCG (SEQ ID NO: 11) |
|   | NASP | GIG ACC AAC CIC ITC CAG (SEQ ID NO: 12) |
| P | PSP | GCT CIA GIG TGC GAC TGT G (SEQ ID NO: 13) |
|   | PASP | GCT CAG ACA GGT TCT TAT TG (SEQ ID NO: 14) |
| M | MSP | GIT GAA CCC TAG GAG AAC TC (SEQ ID NO: 15) |
|   | MASP | GIA TGC AGG TGG TTG AGG (SEQ ID NO: 16) |
| G | GSP | GCT CCA ATC CIC TCT CCI AT (SEQ ID NO: 17) |
|   | GASP | GAC TGA GAG GGA ACT CAA (SEQ ID NO: 18) |
| X | 320-SP1 | CACATCTAGAGCTTGAAGACC (SEQ ID NO: 9) |
|   | 320-ASP1 | ACCATCACAGCCAGTGCTG (SEQ ID NO: 10) |
| L | Mono-1 | GGCAAGGCTGTTTGGATTACTGA CC (SEQ ID NO: 1) |
|   | Mono-2 | ACAGGTTTGCAGCTAAGGAGGAC A (SEQ ID NO: 2) |

Figure 22:
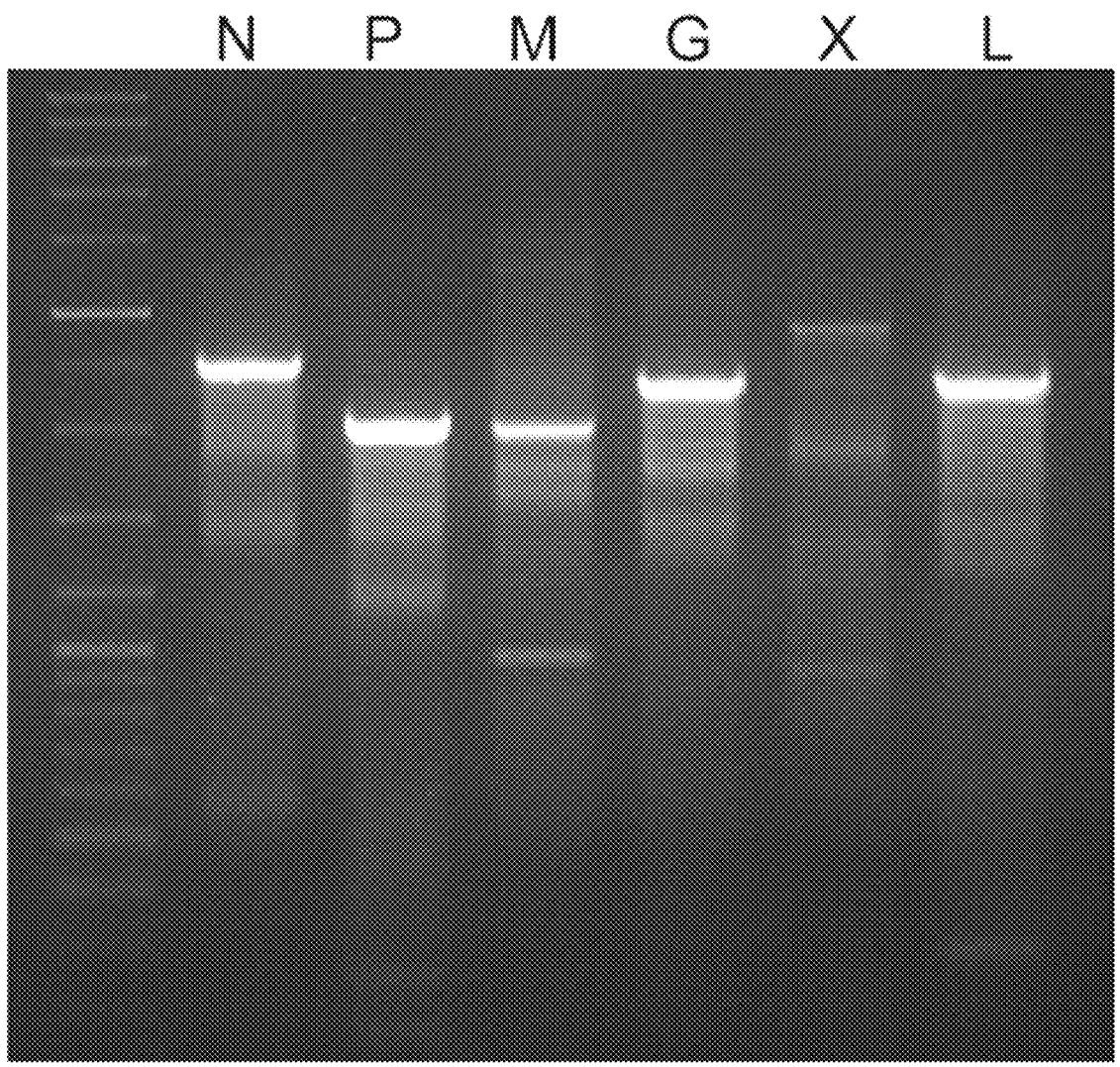
FIG. 22: Sf-rhabdovirus in BmN cells. Total RNA was extracted from the BmN cell line, derived from the lepidopteran insect, *Bombyx mori*, as described in Example 4. Samples were then assayed for various Sf-rhabdovirus RNAs (N, P, M, G, X, and L) by RT-PCR, as described in Example 22.

As seen in FIG. 22, amplicons corresponding to all six Sf-rhabdovirus genes (N, P, M, G, X, and L) were observed. These results demonstrated that the BmN cell line, which is derived from the lepidopteran insect, *Bombyx mori*, a close relative of *S. frugiperda*, is also infected with Sf-rhabdovirus.

Collectively our results suggest many established cell lines may be infected with a virus. This may be due to persistent virus infection of the organisms from which these cell lines are derived. Our results also demonstrate the disclosed methods for obtaining established lines are broadly applicable.

The recent surge of regulatory agency approvals for the use of BIGS-derived biologics in human and veterinary patients is a critically important milestone in the emergence of the BIGS as a bona fide commercial biologics manufacturing platform. However, the discovery of infectious viral contaminants in the insect cell lines most frequently used as hosts for baculovirus vectors, including Sf and Tn cells raises questions about the safety of BIGS-produced biologics. In this context, it is important to emphasize that there is no evidence that Sf-rhabdovirus or Tn-nodavirus pose a clear threat to human or veterinary patients. Nevertheless, the clear response to the identification of any adventitious agent in any biologic manufacturing platform is to eliminate the agent to create an inherently safer system. Thus, we invented Sf-RVN and Tn-NVN, which are not contaminated with Sf-rhabdovirus or Tn-nodavirus, respectively. In fact, both of these cell lines lack any detectable trace of either one of these recently identified viral contaminants.

This conclusion is based on the results of highly sensitive RT-PCR/nested PCR assays, which we used to demonstrate that Sf-RVN cells and cell-free media had no detectable Sf-rhabdovirus and Tn-NVN cells and cell-free media had no detectable Tn-nodavirus RNA over the course of at least 55 passages in our lab. It is strongly supported by the duration of our Sf-rhabdovirus- and Tn-nodavirus-specific RT-PCR/nested PCR testing regimens, which are still underway and, at this time, have revealed no trace of Sf-rhabdovirus in Sf-RVN or Tn-nodavirus in Tn-NVN cells over the course of 170 and 100 serial passages, respectively. If these cells had a low level of Sf-rhabdoviral or Tn-nodaviral contamination, we would expect these viruses to fairly quickly replicate to detectable levels, particularly considering the reportedly high level of contamination ($2\times10^9$ particles/ml of extracellular growth medium) in Sf cell cultures. In addition, we have confirmed and extended our Sf-RVN results by bioinformatic analyses of publically available genomic and transcriptomic data on Sf-21 cells (Geisler and Jarvis, 2016), as well as original genomic and transcriptomic databases obtained by massively parallel sequencing our Sf-RVN cells (Table 2).

Another conclusion from the current teachings is that the essential properties of Sf-RVN and Tn-NVN cells, in context of their potential as alternative hosts for the BIGS, are highly similar to those of Sf9 and TN-368 cells, respectively, which we used as "gold standard" hosts for the BIGS due to their widespread use in the field. We found that neither our Sf-RVN nor our Tn-NVN cells are detectably contaminated with *Mycoplasma*. We also found that the basic growth properties of Sf-RVN and Sf9 and Tn-NVN and TN-368 cells, respectively, examined within the parameters of standard cell culture maintenance protocols, were indistinguishable.

Another conclusion from the current teachings is that Sf-RVN and Tn-NVN cells can function at least as well as their virus-contaminated counterparts as host components of the BIGS. This conclusion was supported by the finding that Sf-RVN and Sf9 and Tn-NVN and TN-368 cells, respectively, supported approximately equal levels of recombinant protein and glycoprotein production, secretion, and enzyme activity. Formally, this conclusion can only be applied to the three different products used as models herein. While we used an intracellular bacterial protein and two secreted human N-glycoproteins in an effort to broaden our analysis, it is possible that Sf-RVN and/or Tn-NVN cells will be found to produce higher or lower levels of other recombinant proteins in the future. We also found that Sf-RVN and Sf9 and Tn-NVN and TN-368 cells, respectively, provided nearly identical N-glycosylation patterns. The conclusion that Sf-RVN and Sf9 and Tn-NVN and TN-368 cells provided nearly identical N-glycosylation patterns formally applies only to hEPO, which was the model used for the analysis. However, compared to potential variation in recombinant protein production levels, Sf-RVN and Sf9 and Tn-NVN and TN-368 are far less likely to differentially N-glycosylate other products because the analytical results obtained with a given product reflect endogenous N-glycan processing capabilities. If they existed, differences in the extent of N-glycan processing would have been detected in our analysis of hEPO glycosylation by the different cell lines.

Figure 11:
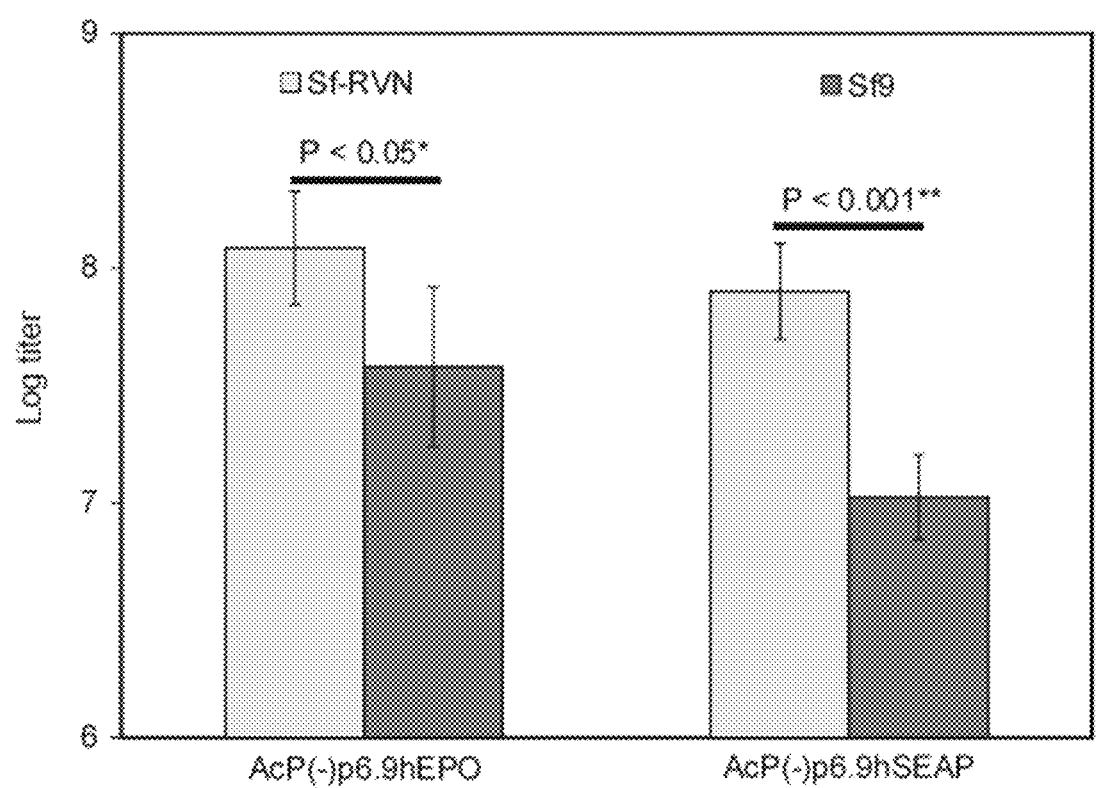
FIG. 11: Recombinant baculovirus production. Sf-RVN and Sf9 cells were infected with Sf-rhabdovirus-free stocks of AcP(−)p6.9hSEAP or AcP(−)p6.9hEPO. The resulting progeny were harvested and titered by plaque assays, as described in Example 11. The resulting titers were plotted as the average viral titers obtained in three independent experiments, with error bars representing confidence intervals depicted as '*' ($P<0.05$) or '**' ($P<0.001$).
Figure 12:
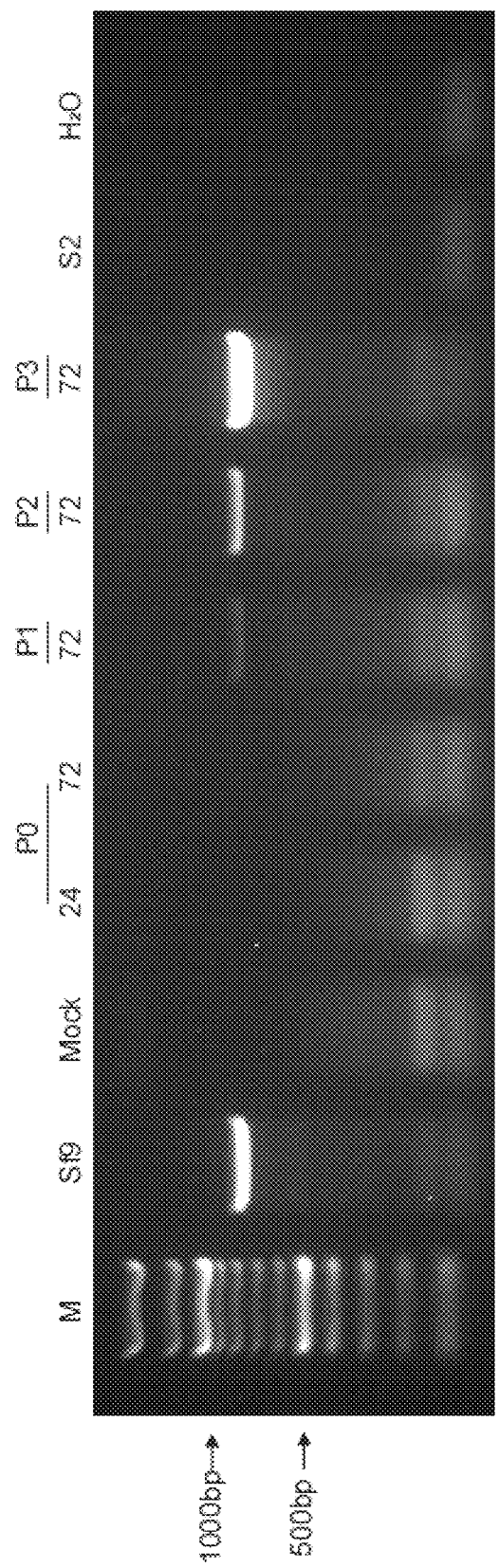
FIG. 12: Sf-rhabdovirus infection of Sf-RVN cells. Sf-RVN cells were mock-infected or infected with cell free medium derived from Sf9 cells, as described in Example 13, and then total RNA was extracted and assayed for Sf-rhabdovirus by RT-PCR, as described in Example 4. The lane marked: M contains base pair markers; Sf9 contains material amplified from Sf9 cell RNA; Mock contains material amplified from Sf-RVN cell RNA obtained after the cells were "mock infected"; PO (24) and (72) contains material amplified from Sf-RVN cell RNA obtained after the cells were infected with Sf-rhabdovirus for 24 and 72 h, respectively; P1 (72), P2 (72) and P3 (72) contain material amplified from Sf-RVN cell RNA obtained 72 h after the first, second, or third time the cells were passaged after being infected with Sf-rhabdovirus, respectively; S2 contains material amplified from S2R+ cell RNA; and H2O contains distilled water.

Another important functional capability of Sf-RVN and Sf9 cells examined in herein was their ability to produce infectious recombinant baculovirus progeny. Surprisingly, we found that Sf-RVN cells produced higher levels of infectious progeny (in some cases five to ten times as much) when used to propagate two different recombinant baculoviruses, as compared to Sf9 cells (FIG. 11). This difference was statistically significant and demonstrates a clear advantage of Sf-RVN cells over Sf9 cells.

Although the disclosed teachings have been described with reference to various applications, methods, and compositions, it will be appreciated that various changes and modifications may be made without departing from the teachings herein. The foregoing examples are provided to better illustrate the present teachings and are not intended to limit the scope of the teachings herein. Furthermore, various presently unforeseen or unanticipated alternatives, modifications, variations or improvements therein may be subsequently made by those skilled in the art which are also intended to be encompassed by the following claims. Certain aspects of the present teachings may be further understood in light of the following claims.

What is claimed is:

1. A method for obtaining a Sf-rhabdovirus free *Spodoptera frugiperda* cell line, comprising:

isolating a cell from a Sf-rhabdovirus-contaminated *Spodoptera frugiperda* organism or from a Sf-rhabdovirus-contaminated *Spodoptera frugiperda* cell line, wherein isolating comprises limiting dilution;

combining the isolated cell with a cell culture media comprising an antiviral compound to form a first culture composition, wherein the antiviral compound is 6-azauridine;

incubating the first culture composition under conditions suitable for the cell to grow and divide, thereby generating a multiplicity of cells;

removing a portion of the multiplicity of cells or the cell culture media and testing for the presence or absence of a virus;

combining at least some of the multiplicity of cells with cell culture media without an antiviral compound to form a second culture composition; and incubating the second culture composition under conditions suitable for the cells to grow and divide, thereby obtaining the Sf-rhabdovirus free cell line.

2. The method of claim 1, wherein the Sf-rhabdovirus-contaminated *Spodoptera frugiperda* cell line comprises Sf21 cells or Sf9 cells.

3. The method of claim 1, wherein the testing comprises (a) RT-PCR, (b) RT-PCR and nested PCR; (c) quantitative RT-PCR; or (d) an antibody-based detection technique.

4. The method of claim 1, wherein the isolating comprises limiting dilution; wherein the antiviral compound is 6-azauridine; and wherein the testing comprises: (a) RT-PCR or (b) RT-PCR and nested PCR.

* * * * *